US010842436B2

(12) United States Patent
Choi et al.

(10) Patent No.: US 10,842,436 B2
(45) Date of Patent: Nov. 24, 2020

(54) ELECTRONIC DEVICE AND BODY COMPOSITION MEASURING METHOD OF ELECTRONIC DEVICE CAPABLE OF AUTOMATICALLY RECOGNIZING BODY PART TO BE MEASURED

(71) Applicant: Samsung Electronics Co., Ltd., Suwon-si (KR)

(72) Inventors: Ah-Young Choi, Seoul (KR); Young-Hyun Kim, Suwon-si (KR); Seong-Wook Jo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 644 days.

(21) Appl. No.: 15/053,277

(22) Filed: Feb. 25, 2016

(65) Prior Publication Data

US 2016/0249857 A1    Sep. 1, 2016

(30) Foreign Application Priority Data

Feb. 26, 2015    (KR) .................. 10-2015-0027606
May 13, 2015    (KR) .................. 10-2015-0066849

(51) Int. Cl.
*A61B 5/00* (2006.01)
*A61B 5/107* (2006.01)
(Continued)

(52) U.S. Cl.
CPC .......... *A61B 5/684* (2013.01); *A61B 5/0537* (2013.01); *A61B 5/067* (2013.01); *A61B 5/1075* (2013.01);
(Continued)

(58) Field of Classification Search
CPC ...................................... A61B 5/684
See application file for complete search history.

(56) References Cited

U.S. PATENT DOCUMENTS

2007/0100252 A1* 5/2007 Chou .............. A61B 5/0537
600/547
2009/0131812 A1 5/2009 Sato et al.
(Continued)

FOREIGN PATENT DOCUMENTS

CN           103781408 A     5/2014
DE   10 2008 054 569 A1    7/2010
(Continued)

OTHER PUBLICATIONS

Chinese Examination report dated Feb. 3, 2020, issued in Chinese Application No. 201680012516.5.

*Primary Examiner* — Daniel L Cerioni
*Assistant Examiner* — Yasmeen S Warsi
(74) *Attorney, Agent, or Firm* — Jefferson IP Law, LLP

(57) ABSTRACT

An electronic device and a method of measuring biometric information by an electronic device are provided. The electronic device includes a position sensor unit configured to detect position information of the electronic device, a body fat measurement unit configured to detect body fat measurement information on an examinee, and a controller configured to determine a body part of the examinee corresponding to a position, at which the body fat measurement information is detected, by using the detected position information and the detected body fat measurement information.

14 Claims, 22 Drawing Sheets

(51) Int. Cl.
*A61B 5/06* (2006.01)
*A61B 5/053* (2006.01)
A61B 8/00 (2006.01)
A61B 8/08 (2006.01)

(52) U.S. Cl.
CPC .......... *A61B 5/4872* (2013.01); *A61B 5/6844* (2013.01); *A61B 5/6898* (2013.01); *A61B 5/4519* (2013.01); *A61B 8/0858* (2013.01); *A61B 8/4245* (2013.01)

(56) References Cited

U.S. PATENT DOCUMENTS

2014/0121564 A1* 5/2014 Raskin ................. A61B 5/0022
600/587
2014/0163333 A1 6/2014 Horseman
2016/0235374 A1* 8/2016 Miller .................. A61B 5/7275

FOREIGN PATENT DOCUMENTS

| | | |
|---|---|---|
| JP | 2005-230120 A | 9/2005 |
| JP | 2011-067344 A | 4/2011 |
| KR | 10-2004-0068852 A | 8/2004 |
| KR | 10-2005-0021789 A | 3/2005 |
| KR | 10-2005-0050992 A | 6/2005 |
| KR | 10-2006-0028230 A | 3/2006 |
| KR | 10-2007-0096599 A | 10/2007 |
| KR | 10-2008-0075527 A | 8/2008 |
| KR | 1039473 B1 | 5/2011 |
| KR | 10-1239340 B1 | 3/2013 |

\* cited by examiner

ELECTRONIC DEVICE AND BODY COMPOSITION MEASURING METHOD OF ELECTRONIC DEVICE CAPABLE OF AUTOMATICALLY RECOGNIZING BODY PART TO BE MEASURED

CROSS-REFERENCE TO RELATED APPLICATIONS

This application claims the benefit under 35 U.S.C. § 119(a) of a Korean patent application filed on Feb. 26, 2015 in the Korean Intellectual Property Office and assigned Serial number 10-2015-0027606 and of a Korean patent application filed on May 13, 2015 in the Korean Intellectual Property Office and assigned Serial number 10-2015-0068849, the entire disclosure of each of which is hereby incorporated by reference.

TECHNICAL FIELD

The present disclosure relates to an electronic device and a method of measuring body composition by an electronic device which can automatically recognize a body part to be measured. More particularly, the present disclosure relates to an electronic device and a method which can automatically recognize and measure body composition without the need to input the measurement part.

BACKGROUND

According to recent increases in interest in health, many people's demands for systematic weight loss and health management through usual body fat measurement have increased. According to the demands, a body fat measuring apparatus, which can provide a systematic and healthy weight loss and determine a health state is lately spotlighted as a next-generation health measuring apparatus of a current scale, which can measure body fat, that is, an amount of body composition included in a human body, and promote the health management through human body analysis, such as muscle quantity, total body water, body fat percentage, and the like. Based on the fact that an electrical current may flow in the human body through water, by applying the current to a body part at which body fat is to be measured and detecting the voltage, the body fat measuring apparatus can measure electrical resistance, that is, impedance of the corresponding body part. The body fat measuring apparatus can calculate various body composition analysis results including muscle quantity, total body water, and body fat percentage of an examinee by using the measured impedance.

Meanwhile, these days, the user or the examinee can measure body part-specific body composition through a portable terminal which can be easily carried and can measure partial body composition of each body part anywhere and at any time. The body composition measuring apparatus may provide information by which a muscle development level of each body part can be determined and, accordingly, may be useful for identifying an effect of exercise on each body part, a left and right balance state, an upper and lower body development level, and an effect of rehabilitation treatment.

However, with a body composition measuring apparatus of the related art, in order to measure partial body fat, a user or an examinee manually inputs a measurement part which is desired to be measured and places the measurement apparatus on the corresponding measurement part. Accordingly, the user or the examinee may feel cumbersomeness and inconvenience to input a body part to be measured every time. Further, when inputting a measurement part which the user or the examinee desires to measure, the user or the examinee should know in advance an accurate name of each measurement part preset in the measuring apparatus, which results in difficulty in use.

Therefore, a need exists for an electronic device and a method of measuring body composition by an electronic device which can automatically recognize a body part to be measured.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure may provide an electronic device and a method which can automatically recognize and measure body composition without the need to input the measurement part.

In accordance with an aspect of the present disclosure, an electronic device for automatically recognizing a measurement body part is provided. The electronic device includes a position sensor unit configured to detect position information of the electronic device related to a body of an examinee, a body fat measurement unit configured to detect body fat measurement information of the body at a position corresponding to the detected position information, and a controller configured to determine a measurement body part corresponding to a position, at which the body fat measurement information is detected, among a plurality of preset body parts by using the detected position information and the detected body fat measurement information.

In accordance with another aspect of the present disclosure, a method of measuring body composition by an electronic device for automatically recognizing a measurement body part is provided. The method includes detecting position information of the electronic device related to a body of an examinee, detecting body fat measurement information of the body at a position corresponding to the detected position information, and determining a measurement body part corresponding to a position, at which the body fat measurement information is detected, among a plurality of preset body parts by using the detected position information and the detected body fat measurement information.

According to various embodiments of the present disclosure, in body composition measurement, it is possible to improve a user's convenience by automatically recognizing and measuring a measurement body part which the user or the examinee desires to measure without the need to manually input the measurement body part.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
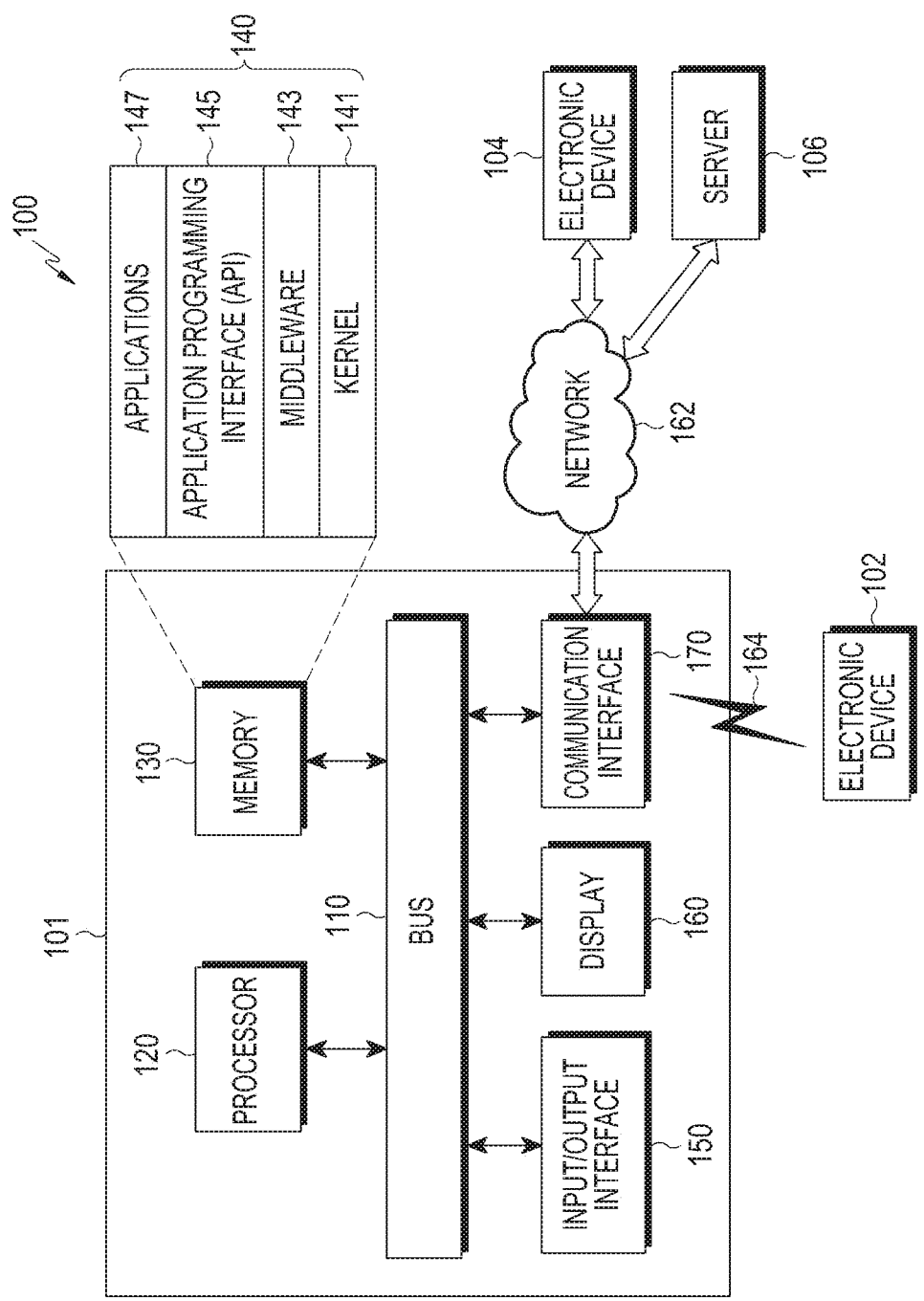
FIG. 1 illustrates a network environment according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the expression "have", "may have", "include", or "may include" refers to the existence of a corresponding feature (e.g., a numeral, a function, an operation, or a constituent element, such as a component), and does not exclude one or more additional features.

In an embodiment of the present disclosure, the expression "A or B", "at least one of A or/and B", or "one or more of A or/and B" may include all possible combinations of the items listed. For example, the expression "A or B", "at least one of A and B", or "at least one of A or B" may include (1) at least one A, (2) at least one B, or (3) both at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

When it is mentioned that one element (e.g., a first element) is "(operatively or communicatively) coupled with/to or connected to" another element (e.g., a second element), it should be construed that the one element is directly connected to the another element or the one element is indirectly connected to the another element via yet another element (e.g., a third element). In contrast, it may be understood that when an element (e.g., the first element) is referred to as being "directly connected," or "directly coupled" to another element (e.g., the second element), there are no element (e.g., the third element) interposed between them.

As used herein, the expression "configured to" may be interchangeably used with the expression "suitable for", "having the capability to", "designed to", "adapted to", "made to", or "capable of". The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g., an embedded processor) only for performing the corresponding operations or a generic-purpose processor (e.g., a central processing unit (CPU) or an application processor (AP)) that can perform the corresponding operations by executing one or more software programs stored in a memory device.

The terms used herein are merely for the purpose of describing particular embodiments and are not intended to limit the scope of other embodiments of the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in an embodiment of the present disclosure. In some cases, even the term defined in an embodiment of the present disclosure should not be interpreted to exclude embodiments of the present disclosure.

An electronic device according to various embodiments of the present disclosure may include at least one of, for example, a smart phone, a tablet personal computer (PC), a mobile phone, a video phone, an electronic book reader (e.g., an e-book reader), a desktop PC, a laptop PC, a netbook computer, a workstation, a server, a personal digital assistant (PDA), a portable multimedia player (PMP), a moving picture experts group (MPEG-1 or MPEG-2) audio layer-3 (MP3) player, a mobile medical device, a camera, a wearable device, and the like. According to various embodiments of the present disclosure, the wearable device may include at least one of an accessory type (e.g., a watch, a ring, a bracelet, an anklet, a necklace, a glasses, a contact lens, or a head-mounted device (HMD)), a fabric or clothing integrated type (e.g., an electronic clothing), a body-mounted type (e.g., a skin pad, or tattoo), and a bio-implantable type (e.g., an implantable circuit).

According to various embodiments of the present disclosure, the electronic device may be a home appliance. The home appliance may include at least one of, for example, a television (TV), a digital video disc (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to an embodiment of the present disclosure, the electronic device may include at least one of various medical devices (e.g., various portable medical measuring devices (e.g., a blood glucose monitoring device, a heart rate monitoring device, a blood pressure measuring device, a body temperature measuring device, and the like), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight DR (FDR), a vehicle infotainment devices, an electronic devices for a ship (e.g., a navigation device for a ship, a gyro-compass, and the like), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, and the like).

According to various embodiments of the present disclosure, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. According to various embodiments of the present disclosure, the electronic device may also be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. In an embodiment of the present disclosure, the term "user" may indicate a person using an electronic device or a device (e.g., an artificial intelligence electronic device) using an electronic device.

FIG. 1 illustrates a network environment according to an embodiment of the present disclosure.

Referring to FIG. 1, an electronic device 101 within a network environment 100, according to various embodiments of the present disclosure, will be described. The electronic device 101 may include a bus 110, a processor 120, a memory 130, an input/output interface 150, a display 160, and a communication interface 170. In various embodiments of the present disclosure, the electronic device 101 may omit at least one of the above elements or may further include other elements.

The bus 110 may include, for example, a circuit for connecting the elements 110 to 170 and transferring communication (for example, control messages and/or data) between the elements.

The processor 120 may include one or more of a CPU, an AP, and a communication processor (CP). The processor 120 may carry out, for example, operations or data processing relating to control and/or communication of one or more other elements of the electronic device 101.

The memory 130 may include a volatile memory and/or a non-volatile memory. The memory 130 may store, for example, instructions or data relevant to at least one other element of the electronic device 101. According to an embodiment of the present disclosure, the memory 130 may store software and/or a program 140. The program 140 may include, for example, a kernel 141, middleware 143, an application programming interface (API) 145, and/or application programs (or "applications") 147. At least some of the kernel 141, the middleware 143, and the API 145 may be referred to as an operating system (OS).

The kernel 141 may control or manage system resources (for example, the bus 110, the processor 120, or the memory 130) used for performing an operation or function implemented by the other programs (for example, the middleware 143, the API 145, or the application programs 147). Furthermore, the kernel 141 may provide an interface through which the middleware 143, the API 145, or the application programs 147 may access the individual elements of the electronic device 101 to control or manage the system resources.

The middleware 143 may function as, for example, an intermediary for allowing the API 145 or the application programs 147 to communicate with the kernel 141 to exchange data.

In addition, the middleware 143 may process one or more task requests received from the application programs 147 according to priorities thereof. For example, the middleware 143 may assign priorities for using the system resources (for example, the bus 110, the processor 120, the memory 130, and the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (for example, instruction) for file control, window control, image processing, or text control.

The input/output interface 150 may function as, for example, an interface that may transfer instructions or data input from a user or another external device to the other element(s) of the electronic device 101. In addition, the input/output interface 150 may output commands or data received from other element(s) of the electronic device 101 to the user or another external device.

The display 160 may include, for example, a liquid crystal display (LCD), a light-emitting diode (LED) display, an organic LED (OLED) display, a microelectromechanical systems (MEMS) display, and an electronic paper display. The display 160 may display, for example, various types of content (for example, text, images, videos, icons, symbols, and the like) to the user. The display 160 may include a touch screen and receive, for example, a touch, gesture, proximity, or hovering input by using an electronic pen or a user's body part.

The communication interface 170 may set, for example, communication between the electronic device 101 and an external device (for example, a first external electronic device 102, a second external electronic device 104, or a server 106). For example, the communication interface 170 may be connected to a network 162 through wireless or wired communication to communicate with the external device (for example, the second external electronic device 104 or the server 106).

The wireless communication may use at least one of, for example, long term evolution (LTE), LTE-advance (LTE-A), code division multiple access (CDMA), wideband CDMA (WCDMA), universal mobile telecommunications system (UMTS), WiBro (Wireless Broadband), and global system for mobile communications (GSM), as a cellular communication protocol. In addition, the wireless communication may include, for example, short range communication 164. The short-range communication 164 may be performed by using at least one of, for example, Wi-Fi, Bluetooth (BT), near field communication (NFC), and global navigation satellite system (GNSS). The GNSS may include at least one of, for example, a GPS, a global navigation satellite system (Glonass), a Beidou navigation satellite system (hereinafter, referred to as "Beidou"), and Galileo (European global satellite-based navigation system). Hereinafter, in an embodiment of the present disclosure, the "GPS" may be interchangeably used with the "GNSS". The wired communication may include at least one of, for example, a universal serial bus (USB), a high definition multimedia interface (HDMI), recommended standard 232 (RS-232), and a plain old telephone service (POTS). The network 162 may include at least one of a communication network, for example, a computer network (for example, a local area network (LAN) or a wide area network (WAN)), the Internet, and a telephone network.

Each of the first external electronic device 102 and the second external electronic device 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be performed in another electronic device or a plurality of electronic devices (for example, the first external electronic device 102, the second external electronic device 104, or the server 106). According to an embodiment of the present disclosure, when the electronic device 101 has to perform some functions or services automatically or in response to a request, the electronic device 101 may make a request for performing at least some functions relating thereto to another device (for example, the first external electronic device 102, the second external electronic device 104, or the server 106) instead of performing the functions or services by itself or in addition. Another electronic device (for example, the first external electronic device 102, the second external electronic device 104, or the server 106) may execute the requested functions or the additional functions, and may deliver a result of the execution to the electronic device 101. The electronic device 101 may process the received result as it is or perform additional processing to provide the requested functions or services. To achieve this, for example, cloud computing, distributed computing, or client-server computing technology may be used.

Figure 2:
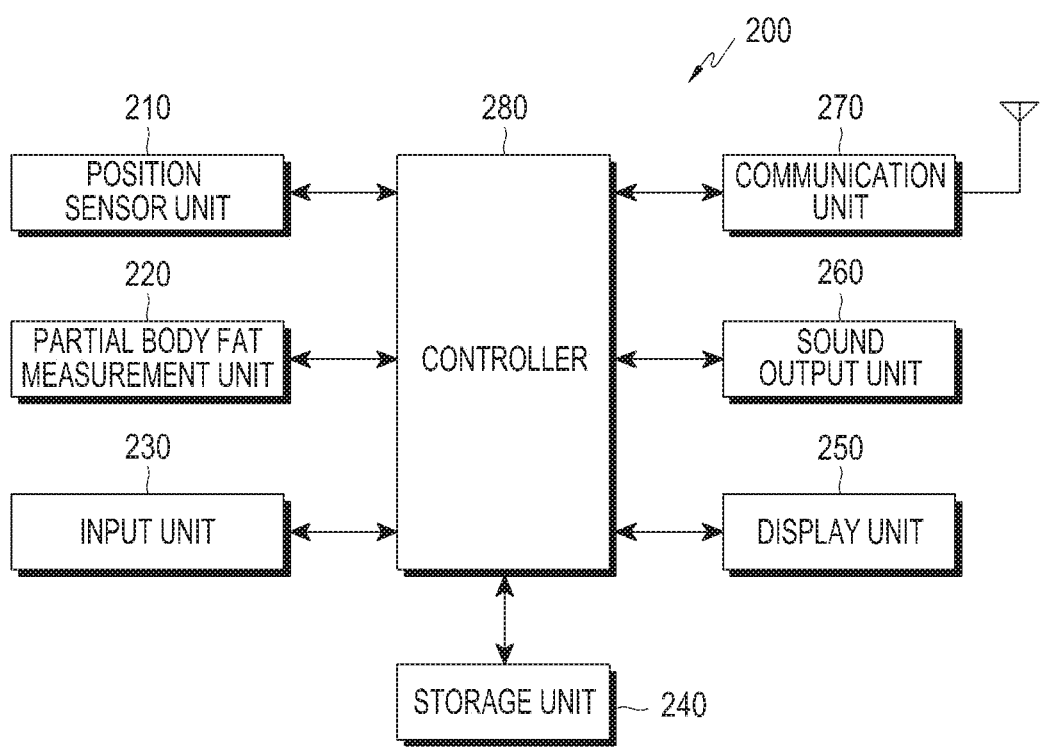
FIG. 2 is a block diagram schematically illustrating an electronic device which can automatically recognize a measurement body part according to an embodiment of the present disclosure.

FIG. 2 is a block diagram schematically illustrating an electronic device which can automatically recognize a measurement body part according to an embodiment of the present disclosure.

Referring to FIG. 2, an electronic device 200 may include, for example, all or some of the electronic device 101 illustrated in FIG. 1. The electronic device 200 according to an embodiment of the present disclosure may include a position sensor unit 210, a partial body fat measurement unit 220, and a controller 280. The electronic device 200 may further include an input unit 230, a storage unit 240, a display unit 250, a sound output unit 260, and a communication unit 270.

The position sensor unit 210 may detect position information of the electronic device 200 which is related to an examinee's body. The position sensor unit 210 may detect position information at, for example, a reference position and a measurement position. The reference position may refer to a position of the electronic device 200 corresponding to a preset reference body part when body composition of the examinee is measured, and may correspond to, for example, a position of the electronic device 200 at the moment when a body composition measurement application is executed or a position of the electronic device 200 at the moment when the application is executed and a measurement start button 802 (see FIG. 8A) is pressed. The measurement position may correspond to a position of the electronic device 200 corresponding to a measurement body part which the examinee desires to measure among a plurality of preset body parts.

The position sensor unit 210 may include a plurality of position-based sensors and may detect position information of the electronic device 200 from each of the plurality of position-based sensors. According to an embodiment of the present disclosure, the position information may include acceleration values, geomagnetic values and/or altitude values of the electronic device 200 at the reference position and the measurement position. Further, the position information may include position-based detection values detected from all the position-based sensors, such as gyro detection values, angular speed detection values, and motion detection values of the electronic device 200 at the reference position and the measurement position, but are not limited thereto. The controller 280 may determine a position and an attitude of the electronic device 200 at the measurement position moved to from the reference position based on position information of the electronic device 200 at the reference position and the measurement position detected by the position sensor 210.

The partial body fat measurement unit 220 may detect body fat measurement information of the examinee's body at a position corresponding to the position information detected by the position sensor unit 210. For example, the partial body fat measurement unit 220 may detect body fat measurement information related to body fat at the measurement position corresponding to a measurement body part which the examinee desires to measure.

The partial body fat measurement unit 220 may include a plurality of body fat measurement modules and may detect body fat measurement information of the measurement body part corresponding to the measurement position through each of the plurality of body fat measurement modules. According to an embodiment of the present disclosure, the body fat measurement information may include at least one of an impedance value, a skin conductivity value, and a subcutaneous fat thickness. Further, the body fat measurement information is not limited thereto and may include body fat measurement values detected by all the other body fat measurement modules. The controller 280 may determine a measurement body part corresponding to the position where the body fat measurement information is detected based on the position information detected by the position sensor unit 210 and the body fat measurement information detected by the partial body fat measurement unit 220.

The input unit 230 may receive various input signals generated or input by the user or examinee. According to an embodiment of the present disclosure, the input unit 230 may include a key pad, a touch pad, and a voice input module, such as a microphone. Further, the input unit 230 is not limited thereto and may include all input means which can make an input into the electronic device 200 according to an embodiment of the present disclosure.

The storage unit 240 may store in advance basic information, such as a name, age, gender, height, and weight of the examinee and a plurality of body part-specific body fat-based standard ranges according to an age, gender, and height of the examinee. According to an embodiment of the present disclosure, the plurality of body part-specific body fat-based standard ranges may include at least one of a body part-specific impedance standard range, a body part-specific skin conductivity standard range, and a body part-specific subcutaneous fat thickness.

The display unit 250 may display a measurement body part determined by a control of the controller 280 and an analysis result of body composition of the corresponding measurement body part on a screen. Further, the display unit 250 may display a plurality of measurement body parts, each of which is determined by the control of the controller 280 and a combined body composition analysis result based on partial body composition analysis results of the corresponding measurement body parts.

The communication unit 270 may receive information required for measuring the body composition according to the present disclosure from the outside. For example, the communication unit 270 may receive a body part-specific impedance standard range, body part-specific skin conductivity standard range, and body part-specific subcutaneous fat thickness standard range according to an age, gender, and height of the examinee from the outside (for example, the server 106).

The controller 280 may overall control the electronic device 200 according to an embodiment of the present disclosure. The controller 280 may determine a measurement body part which the examinee desires to measure among a plurality of preset body parts based on position information of the electronic device 200 detected through the position sensor unit 210 and body fat measurement information detected through the partial body fat measurement unit 220, that is, a measurement body part corresponding to a position where the body fat measurement information is detected. Further, the controller 280 may analyze a body composition of the determined measurement body part by using the detected body fat measurement information.

According to an embodiment of the present disclosure, the controller 280 may analyze a combined body composition by using body fat measurement information of the measurement body parts determined with respect to some or all of the plurality of preset body parts.

According to an embodiment of the present disclosure, the controller 280 can measure body composition by using a voice recognition function. The controller 280 may receive and recognize an input of the measurement body part which the user or examinee desires to measure through a voice. When the user or examinee brings measurement electrodes A, B, C, and D (see FIG. 4B) of the electronic device 200 into contact with the measurement body part to be measured, the measurement body part corresponding to the contacted measurement position may be determined. In this case, the controller 280 may determine whether the measurement body part recognized through the voice input matches the measurement body part determined using the position information and the body fat measurement information detected through the position sensor unit 210 and the partial body fat measurement unit 220. When the measurement body part recognized through the voice input matches the determined measurement body part, the controller 280 may measure a body composition of the determined measurement body part. Meanwhile, when the measurement body part recognized through the voice input does not match the determined measurement body part, the controller 280 may control the sound output unit 260 to output at least one of a warning sound and a warning comment which informs that the body measurement position of the electronic device 200 is incorrect or control the display unit 250 to display a warning message. The controller 280 may display, on the display unit 250, a guide screen which guides the measurement body part to induce the user to accurately place the measurement electrodes (for example, A, B, C, and D) (see FIG. 4B) of the electronic device 200 at the position corresponding to the measurement body part recognized through the voice input.

According to an embodiment of the present disclosure, the controller 280 can measure body composition by using a touch recognition function. The controller 280 may receive and recognize an input of the measurement body part which the user or examinee desires to measure through a touch input. For example, the controller 280 may receive a plurality of touch inputs of the measurement body parts selected by the user or the examinee through the input unit 230, such as a plurality of selection buttons 1602a and 1602b (see FIGS. 16A and 16B) for selecting the measurement body parts from which the user or the examinee desires to measure a partial body composition on the screen of the display unit 250. When the user or examinee brings the measurement electrodes (for example, A, B, C, and D) (see FIG. 4B) of the electronic device 200 into contact with the measurement body part to be measured while maintaining the touch input after the touch input for the corresponding measurement body part or in a state of pressing the selection button 1602a or 1602b corresponding to corresponding measurement body part, the measurement body part corresponding to the contacted measurement position may be determined. In this case, the controller 280 may determine whether the measurement body part recognized through the touch input matches the measurement body part determined using the position information and the body fat measurement information detected through the position sensor unit 210 and the partial body fat measurement unit 220. When the measurement body part recognized through the touch input matches the determined measurement body part, the controller 280 may measure body composition of the determined measurement body part. Meanwhile, when the measurement body part recognized through the touch input does not match the determined measurement body part, the controller 280 may control the sound output unit 260 to output at least one of a warning sound and a warning comment which informs that the body measurement position of the electronic device 200 is incorrect or control the display unit 250 to display a warning message. The controller 280 may display, on the display unit 250, a guide screen which guides the body measurement position to induce the user to accurately place the measurement electrodes of the electronic device 200 at the position corresponding to the measurement body part recognized through the voice input.

Figure 3:
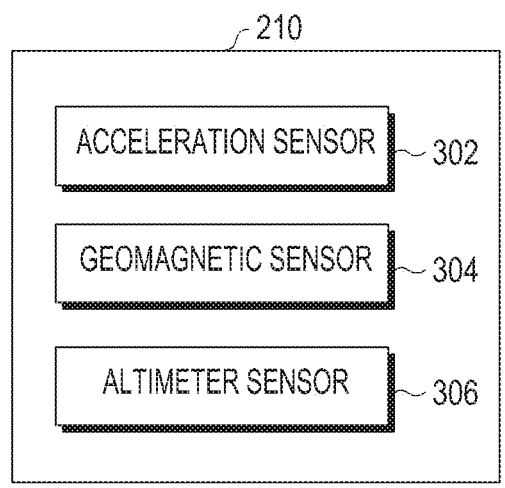
FIG. 3 is a block diagram illustrating a position sensor unit according to an embodiment of the present disclosure.
Figure 4A:
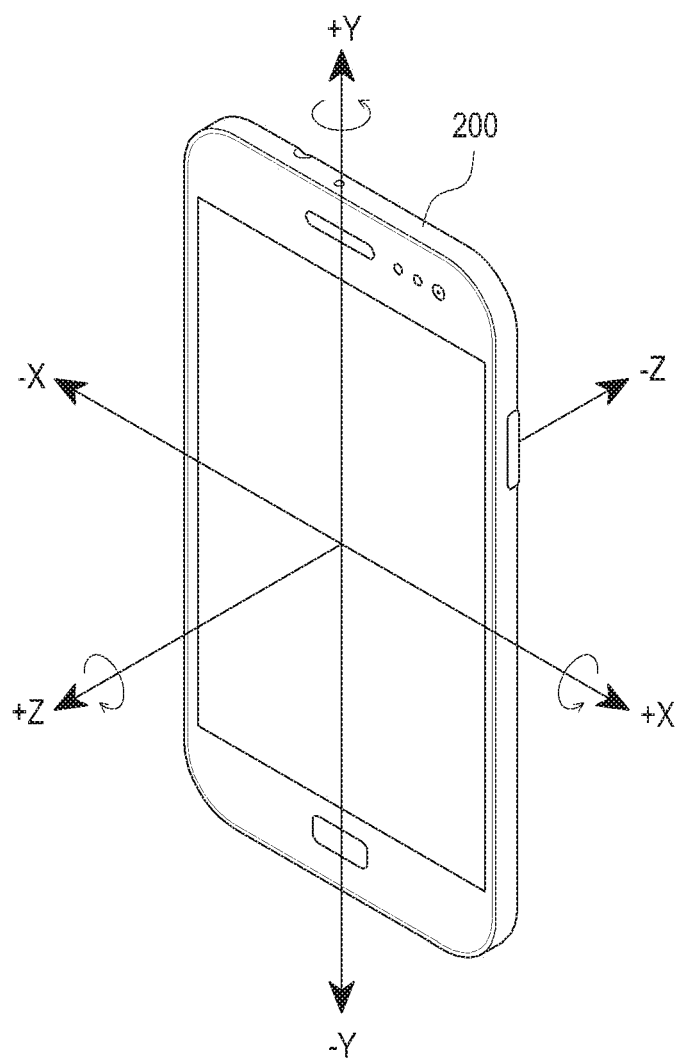
FIG. 4A illustrates reference directions of a position sensor unit according to an embodiment of the present disclosure.
Figure 4B:
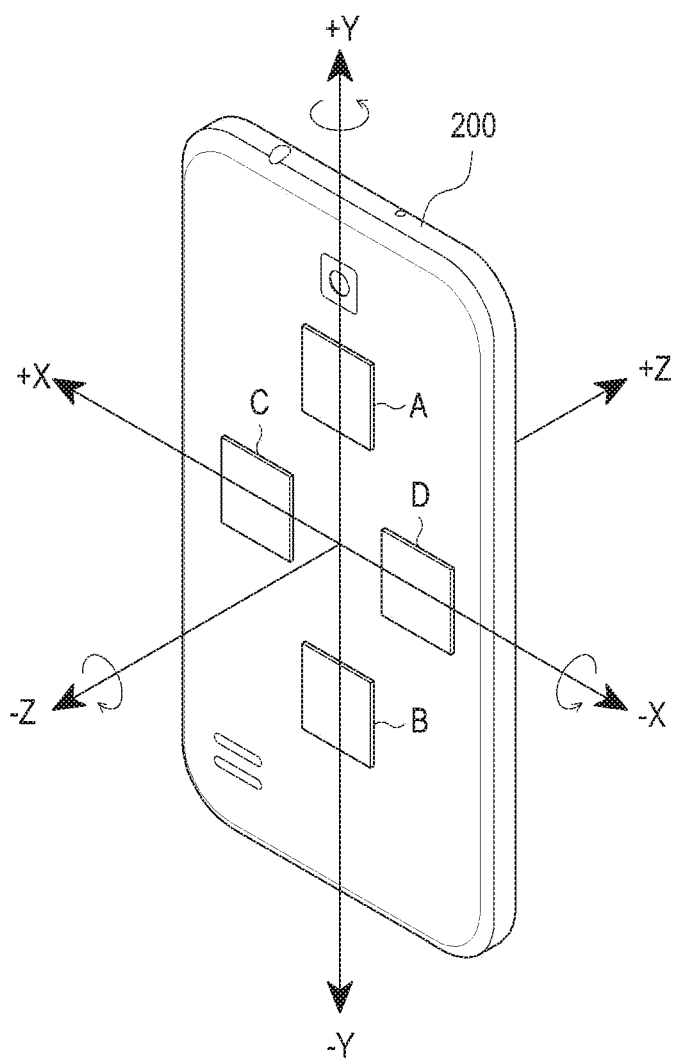
FIG. 4B illustrates measurement electrodes according to an embodiment of the present disclosure.

FIG. 3 is a block diagram of a position sensor unit according to an embodiment of the present disclosure, FIG. 4A illustrates reference directions of a position sensor unit according to an embodiment of the present disclosure, and FIG. 4B illustrates measurement electrodes according to an embodiment of the present disclosure.

Referring to FIGS. 3, 4A, and 4B, the position sensor unit 210 may include at least one of an acceleration sensor 302, a geomagnetic sensor 304, and an altimeter sensor 306.

The acceleration sensor 302 may detect an acceleration at a certain position when the electronic device 200 moves. According to the present disclosure, the acceleration sensor 302 may have three axes including a Y axis corresponding to a major axis length direction of the electronic device 200 based on the center of the electronic device 200, an X axis corresponding to a minor axis length direction of the electronic device 200, and a Z axis corresponding to a direction orthogonal to the plane (for example, the screen) with the X axis and the Y axis as illustrated in FIG. 4A, and it is assumed that directions of the X axis, the Y axis, and the Z axis of the electronic device 200 are set as reference directions in a state where the Y axis is orthogonal to the horizontal plane, and the X axis and the Z axis are parallel to the horizontal plane. For example, the acceleration sensor 302 may have reference directions including an upward direction from the center of the electronic device 200, which is a +Y axis (a direction opposite thereto is a Y axis), a rightward direction from the center of the electronic device 200, which is a +X (a direction opposite thereto is an X axis), and a forward direction from the center of the electronic device 200, which is a +Z axis (a direction opposite thereto is a Z axis).

The geomagnetic sensor 304 may detect a direction angle of the electronic device 200 by Earth's magnetic field at a certain measurement position where the electronic device 200 is positioned. According to the present disclosure, the geomagnetic sensor 304 may have three axes equal to those of the acceleration sensor 302 and have reference angles having rotation angles (that is, direction angles) (for example, a pitch angle, a roll angle, and a yaw angle) of 0 degrees with respect to the X axis, the Y axis, and the Z axis of the electronic device 200 in a state where the Y axis is orthogonal to the horizontal plane and the X and Z axes are parallel to the horizontal plane as illustrated in FIG. 4A. The controller 280 may determine an attitude angle of the electronic device 200 through the geomagnetic detection value detected by the geomagnetic sensor 304.

The altimeter sensor 306 may detect an altitude (height) of the electronic device 200 by an air pressure at a certain measurement position of the electronic device 200.

When the electronic device 200 moves to a certain measurement position from a certain reference position, the controller 280 may determine a movement speed, a movement distance, and a movement direction of the electronic device 200 from the reference position to the measurement position by using the acceleration values detected by the acceleration sensor 302 at the reference position and the measurement position. For example, the controller 280 may determine a left and right movement position of the electronic device 200 at the measurement position from the reference position through the determined movement speed, movement distance, and movement direction.

The controller 280 may determine an attitude angle of the electronic device 200 at the measurement position by using the geomagnetic values detected by the geomagnetic sensor 304 at the reference position and the measurement position. For example, the controller 280 may determine a front and back movement position of the electronic device 200 at the measurement position from the reference position through the determined attitude angle.

The controller 280 may determine an altitude of the electronic device 200 at the measurement position by using the altitude values detected by the altimeter sensor 306 at the reference position and the measurement position. For example, the controller 280 may determine an up and down movement position of the electronic device 200 at the measurement position from the reference position through the determined altitude.

As described above, the controller 280 may determine the position and the attitude of the electronic device 200 at the measurement position moved to from the reference position based on at least one of the movement speed, the movement distance, the movement direction, the attitude angle, and the altitude of the electronic device 200 at the measurement position determined using the position information (for example, at least one of the acceleration detection values, the geomagnetic detection values, and the altitude detection values at the reference position and the measurement position) at the reference position and the measurement position detected by the position sensor unit 210.

Although it is illustrated that the position sensor unit 210 includes the acceleration sensor 302, the geomagnetic sensor 304, and the altimeter sensor 306 in FIG. 3, the present disclosure is not limited thereto and the position sensor unit 210 may include all position-based sensors, such as a gyro sensor, an angular speed sensor, and a motion sensor.

Figure 5:
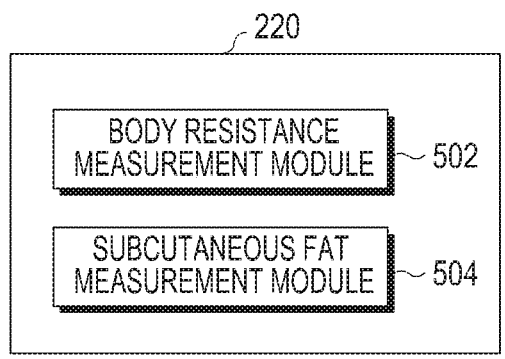
FIG. 5 is a block diagram illustrating a partial body fat measurement unit according to an embodiment of the present disclosure.

FIG. 5 is a block diagram illustrating a partial body fat measurement unit according to an embodiment of the present disclosure.

Referring to FIG. 5, the partial body fat measurement unit 220 may include a body resistance measurement module 502 and a subcutaneous fat measurement module 504. The body resistance measurement module 502 and the subcutaneous fat measurement module 504 may be connected to certain measurement electrodes A, B, C, and D as illustrated in FIG. 4B. The certain measurement electrodes A, B, C, and D may be switched through a certain switching unit and connected to the corresponding measurement module to be used in common when the body resistance or the subcutaneous fat is measured. Although FIG. 4B illustrates that the certain measurement electrodes A, B, C, and D are used in common for the body resistance measurement module 502 and the subcutaneous fat measurement module 504, the present disclosure is not limited thereto and certain measurement electrodes may be connected to each of the body resistance measurement module 502 and the subcutaneous fat measurement module 504.

The body resistance measurement module 502 may detect a size of the body resistance according to an amount of body fat of a measurement body part which the examinee desires to measure. The body resistance measurement module 502 may measure two types of body resistance according to a measurement method. For example, the body resistance measurement module 502 may apply an alternating current (AC) to pass through the measurement body part through two electrodes (for example, A and B) (see FIG. 4B), which contact the measurement body part, and measure an AC voltage when the AC passes through the measurement body part through the other two electrodes (for example, C and D) (see FIG. 4B), which contact the measurement body part. The body resistance measurement module 502 may detect an impedance value [Ω] of the corresponding measurement body part calculated using the AC applied to the measurement body part and the AC voltage measured from the measurement body part. The AC applied to the measurement body part may have, for example, a range about from 1 KHz to 1 GHz. The impedance value may have different impedance standard ranges according to the measurement body part. Further, the body resistance measurement module 502 may detect the impedance value by using a phase delay of the AC applied to the measurement body part and the detected AC voltage. When it is assumed that a minimum electrode configuration (at least four) for impedance measurement corresponds to one measurement channel, the body resistance measurement module 502 according to an embodiment of the present disclosure may have at least one impedance measurement channel and measure the impedance of at least one measurement body part at one time by using at least one impedance measurement channel. When the electronic device 200 has at least one impedance measurement channel, the electronic device 200 may further include at least one position sensor unit corresponding to each measurement channel. The controller 280 may distinguish measurement body parts according to the impedance value detected by the body resistance measurement module 502 and analyze a partial body composition of the corresponding measurement body part by using the impedance value.

The body resistance measurement module 502 may apply a direct current (DC) to pass through the measurement body part through two electrodes (for example, A and B) (see FIG. 4B), which contact the measurement body part, and measure a DC voltage when the DC passes through the measurement body part through the other two electrodes (for example, C and D) (see FIG. 4B), which contact the measurement body part. The body resistance measurement module 502 may detect a skin conductivity value [Ω] of the corresponding measurement body part calculated using the DC applied to the measurement body part and the DC voltage measured from the measurement body part. For example, the skin conductivity refers to a measurement value of a temporary change of electric resistance detected by a weak electric signal (DC) applied to the measurement body part and may have different skin conductivity standard ranges according to the contact part, that is, the measurement body part. The controller 280 may distinguish contact parts of the measurement electrodes A, B, C, and D (see FIG. 4B), that is, the measurement body parts according to the skin conductivity value detected by the body resistance measurement module 502.

The subcutaneous fat measurement module 504 may detect a thickness of the subcutaneous fat according to an amount of body fat of a measurement body part which the examinee desires to measure. The subcutaneous fat measurement module 504 may detect the thickness of the subcutaneous fat of the corresponding to measurement body part through various measurement methods (for example, by using a radio frequency (RF) signal, ultrasonic waves, or a light source). For example, when the subcutaneous fat is measured using the RF signal, the subcutaneous fat measurement module 504 may apply an RF signal having a frequency of about 0.1 to 200 GHz to the measurement body part through the measurement electrodes (for example, A and B) (see FIG. 4B) and measure the reflected and returned RF signal, which has been absorbed into the body fat of the measurement body part, through the measurement electrodes (for example, C and D) (see FIG. 4B), so as to detect a subcutaneous fat thickness of the measurement body part. The detected thickness of the subcutaneous fat may have different subcutaneous fat thickness standard ranges according to the measurement body part.

Since the impedance value, the skin conductivity value, and the subcutaneous fat thickness may have different standard ranges according to the body part, the controller 280 may determine at least one candidate measurement body part corresponding to the detected body fat measurement information among a plurality of preset body parts by using the body fat measurement information including at least one of the impedance value, the skin conductivity value, and the subcutaneous fat thickness, detected by the partial body fat measurement unit 220. An example of a plurality of body part-specific body fat-based standard ranges is schematized in Table 1 below.

TABLE 1

|  | Torso (TR) | Right arm (RA) | Left arm (LA) | Right leg (RL) | Left leg (LL) |
|---|---|---|---|---|---|
| Impedance [Ω] | 10~50 | 300~500 | 300~500 | 200~300 | 200~300 |
| Skin conductivity [Ω] | 1-9M | 50~70M | 50~70M | 65~90M | 65~90M |
| Subcutaneous fat thickness [mm] | 10-30 | 4~15 | 4~15 | 5~17 | 5~17 |

As shown in Table 1, the plurality of body part-specific (for example, torso (TR), arm (RA or LA), and leg (RL or LL)) body fat-based standard ranges (for example, body part-specific impedance, body part-specific skin conductivity, and body part-specific subcutaneous fat thickness) may vary depending on an age, gender, and height of the examinee. The plurality of body part-specific body fat-based standard ranges according to the age, gender, and height may be stored in advance in the storage unit 240 or downloaded from the outside (for example, the server 106) through the communication unit 270 and stored in the storage unit 240.

Although the present disclosure sets the plurality of preset body parts as a total of five measurement body parts including the torso (TR) and the left and right arms/legs (LA and RA/LL and RL) for convenience of the description (see FIG. 11A), the measurement body parts may be further subdivided. For example, the measurement body parts may be preset as left and right chests, abdomen, left and right upper arms, left and right lower arms, left and right thighs, and left and right calves (see FIG. 11B). As the measurement body parts are further subdivided, a partial body composition can be measured more accurately.

Figure 6:
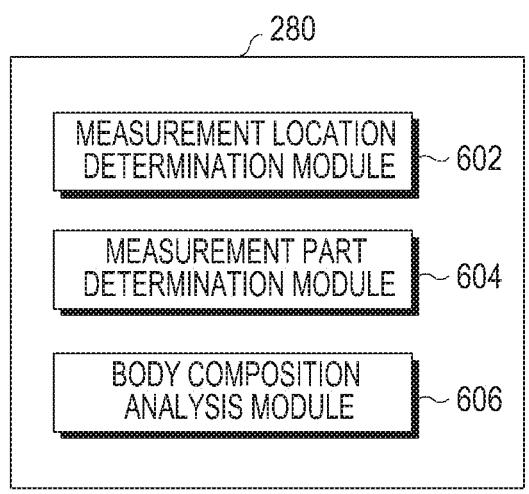
FIG. 6 is a block diagram illustrating a controller according to an embodiment of the present disclosure.

FIG. 6 is a block diagram illustrating a controller according to an embodiment of the present disclosure.

Referring to FIG. 6, the controller 280 may include a measurement position determination module 602, a measurement part determination module 604, and a body composition analysis module 606.

The measurement position determination module 602 may determine a position and an attitude of the electronic device 200 at a measurement position corresponding to a measurement body part based on position information of the electronic device 200 (for example, an acceleration value, a geomagnetic value, and an altitude value of the electronic device 200 at a position corresponding to a reference body part and a measurement body part) related to the examinee's body detected by the position sensor unit 210.

More specifically, when the measurement of partial body fat starts, the measurement position determination module 602 may detect acceleration values, geomagnetic values, and altitude values of the electronic device 200 through the position sensor unit 210 for an initial setting time (for example, about 1 second) after the measurement starts, calculate an average value of each, and set the calculated average acceleration value, average geomagnetic value, average altitude value as reference values corresponding to the position information of the electronic device 200 at the reference position. At this time, the reference body part corresponding to the reference position may be preset by default. For example, when the reference body part is preset as the abdomen by default, it is assumed that the user places the electronic device 200 on the examinee's abdomen for the body composition measurement and starts the body composition measurement. The reference body part corresponding to the reference position may be preset by an input of the user or the examinee. For example, the user or the examinee may preset the reference body part corresponding to the reference position by inputting a voice through the input unit 230, such as a microphone, a keypad, and a touch pad or selecting a measurement body part displayed on the display unit 250 before the body composition measurement.

The measurement position determination module 602 may detect position information of the electronic device 200 at a reference position corresponding to a preset reference body part and position information of the electronic device 200 at a measurement position from which the partial body composition is measured among the examinee's body parts through the position sensor unit 210 after the body composition measurement starts.

The measurement position determination module 602 may determine a movement speed, a movement distance, and a movement direction of the electronic device 200 at the measurement position moved to from the reference position by using the position information (for example, average acceleration value) at the reference position and the position information (for example, acceleration value) at the measurement position detected by the position sensor unit 210.

The measurement position determination module 602 may determine an attitude angle of the electronic device 200 at the measurement position moved to from the reference position by using the position information (for example, average geomagnetic value) at the reference position and the position information (for example, geomagnetic value) at the measurement position detected by the position sensor unit 210.

The measurement position determination module 602 may determine an altitude of the electronic device 200 at the measurement position moved to from the reference position by using the position information (for example, average altitude value) at the reference position and the position information (for example, altitude value) at the measurement position detected by the position sensor unit 210.

The measurement position determination module 602 may determine a position and an attitude of the electronic device 200 at the measurement position based on at least one of the movement distance, the movement direction, the attitude angle, and the altitude of the electronic device 200 at the determined measurement position. It is assumed that the preset reference body part corresponding to the reference position is the examinee's abdomen in an embodiment of the present disclosure.

The measurement part determination module 604 may determine a measurement body part at the measurement position based on the body fat measurement information at the measurement position detected by the partial body fat measurement unit 220 and the position and the attitude of the electronic device 200 at the measurement position determined by the measurement position determination module 602 using the position information at the reference position and the measurement position detected by the position sensor unit 210.

The measurement part determination module 604 may compare the body fat measurement information detected from the measurement body part corresponding to the measurement position with each of the plurality of pre-stored body part-specific body fat-based standard ranges and determine, as at least one candidate measurement body part at the measurement position, at least one measurement body part having the detected body fat measurement information, which is included in the plurality of pre-stored body part-specific body fat-based standard ranges in common among the plurality of preset body parts.

The measurement part determination module 604 may compare the impedance value of the detected body fat measurement information with the body part-specific impedance standard range among the plurality of pre-stored body part-specific body fat-based standard ranges, and select at least one first measurement body part having the detected impedance value, which corresponds to the pre-stored body part-specific impedance standard range, among the plurality of preset body parts.

The measurement part determination module 604 may compare the skin conductivity value of the detected body fat measurement information with the body part-specific skin conductivity standard range among the plurality of pre-stored body part-specific body fat-based standard ranges, and select at least one second measurement body part having the detected skin conductivity value, which corresponds to the pre-stored body part-specific skin conductivity standard range, among the plurality of preset body parts.

The measurement part determination module 604 may compare the subcutaneous fat thickness of the detected body fat measurement information with the body part-specific subcutaneous fat thickness standard range among the plurality of pre-stored body part-specific body fat-based standard ranges, and select at least one third measurement body part having the detected subcutaneous fat thickness, which corresponds to the pre-stored body part-specific subcutaneous fat thickness standard range, among the plurality of preset body parts.

The measurement part determination module 604 may determine, as at least one candidate measurement body part, at least one measurement body part included in the first to third measurement body parts in common among the plurality of preset body parts.

For example, when the impedance value, the skin conductivity value, and the subcutaneous fat thickness detected by the partial body fat measurement unit 220 are 300 Ω, 80M Ω, and 5 mm, the measurement part determination module 604 may compare the detected body fat information with each of the plurality of pre-stored body part-specific body fat-based standard ranges shown in Table 1 and determine at least one candidate measurement body part.

More specifically, the measurement part determination module 604 may compare the impedance value (for example, 300Ω) detected from the measurement body part corresponding to the measurement position with the pre-stored body part-specific impedance standard range and select, as the first measurement body part, at least one measurement body part having the detected impedance value, which corresponds to the pre-stored body part-specific impedance standard range. For example, the first measurement body part may include, for example, left and right arms (RA and LA) or left and right legs (RL and LL).

The measurement part determination module 604 may compare the subcutaneous fat thickness (for example, 5 mm) detected from the measurement body part corresponding to the measurement position with the pre-stored body part-specific subcutaneous fat thickness standard range and select, as the second measurement body part, at least one measurement body part having the detected subcutaneous fat thickness, which corresponds to the pre-stored body part-specific subcutaneous fat thickness standard range. For example, the second measurement body part may include, for example, left and right arms (RA and LA) or left and right legs (RL and LL).

The measurement part determination module 604 may compare the skin conductivity value (for example, 80 MΩ) detected from the measurement body part corresponding to the measurement position with the pre-stored body part-specific skin conductivity standard range and select, as the third measurement body part, at least one measurement body part having the detected skin conductivity value, which corresponds to the pre-stored body part-specific skin conductivity standard range. For example, the third measurement body part may include, for example, left and right legs (RL and LL).

The measurement part determination module 604 may determine, as at least one candidate measurement body part corresponding to the measurement position, at least one selected measurement body part included in the first to third measurement body parts in common based on a result of the comparison between the detected body fat measurement information and each of the pre-stored body part-specific body fat-based standard ranges. For example, the measurement part determination module 604 may determine left and right legs (RL and LL) corresponding to the measurement body part included in the first to third measurement body parts in common as at least one candidate measurement body part corresponding to the measurement position.

After determining at least one candidate measurement body part corresponding to the measurement position based on the detected body fat measurement information, the measurement part determination module 604 may finally determine, as the measurement body part corresponding to the measurement position, the measurement body part corresponding to the position and the attitude of the electronic device 200 at the measurement position detected by the measurement position determination module 602, that is, a left and right movement position, a front and back movement position, and an up and down movement position at the measurement position moved to from the reference position among at least one determined candidate measurement body part.

For example, when it is determined that the left and right movement position and the up and down position information determined by the measurement position determination module 602 are moved in a lower left direction from the reference body part (for example, abdomen) corresponding to the reference position, the measurement part determination module 602 may finally determine, as the left leg (LL), the measurement body part corresponding to the position information determined by the measurement position determination module 602 between at least one candidate measurement body part (for example, left and right legs (LL and RL)) since the electronic device 200 moves in the lower left direction from the reference position (for example, abdomen) to the measurement position.

Although only the left and right movement position and the up and down movement position have been considered to determine the position of the electronic device 200 at the measurement position by the measurement position determination module 602 in the above description, it is possible to distinguish and determine measurement body parts further subdivided than the case where the front and back movement positions according to the attitude of the electronic device 200 are also included.

The body composition analysis module 606 may analyze various body compositions with respect to the corresponding measurement body part based on the body fat measurement information detected from the measurement body part corresponding to the measurement position and examinee's basic body information (for example, age, gender, weight, and height). For example, the body composition analysis module 606 may calculate a total thickness (mm), a subcutaneous fat thickness (mm), a muscle quantity (Kg), a muscle quality (MQ), body water (L), a ratio of water between inside and outside the cell, and an obesity level by using the detected body fat measurement information of the measurement body part (for example, impedance value, skin conductivity value, and subcutaneous fat thickness). Further, the body composition analysis module 606 may also analyze a combined body composition by using a result of the partial body compositions analyzed with respect to the measurement body parts. For example, the body composition analysis module 606 may analyze a body water quantity (L), a muscle quantity of the whole body (Kg), a body fat quantity (Kg), a total weight without fat (Kg), a body mass index (BMI), an abdominal obesity level, left and right balance, and top and bottom balance.

Figure 7:
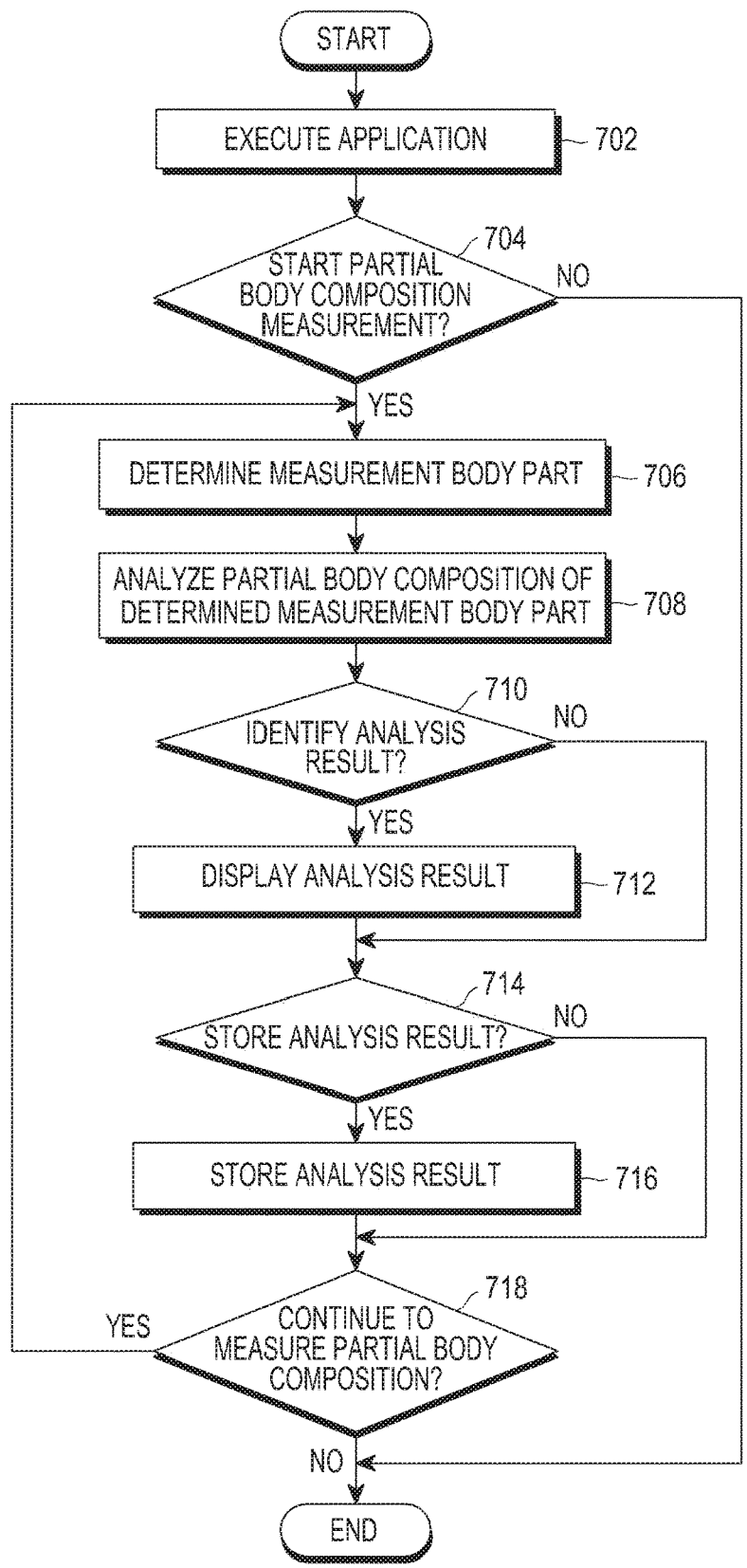
FIG. 7 is a flowchart illustrating a method of measuring body composition by an electronic device which can automatically recognize a measurement body part according to an embodiment of the present disclosure.

FIG. 7 is a flowchart illustrating a method of measuring body composition by an electronic device which can automatically recognize a measurement body part according to an embodiment of the present disclosure.

Referring to FIG. 7, an application for measuring body composition is executed in operation 702. When the application is executed, the controller 280 may determine whether a body composition measurement start signal is input in operation 704. Operation 704 may be omitted when it is considered that the body composition measurement start signal is input when the application is executed.

When the measurement start signal is input in operation 704, the controller 280 may determine the measurement body part corresponding to the measurement position among the plurality of preset body parts based on the position information of the electronic device 200 at the reference position and the measurement position detected by the position sensor unit 210 and the body fat measurement information detected by the partial body fat measurement unit 220 in operation 706.

The controller 280 may analyze a body composition of the determined measurement body part based on the body fat measurement information detected from the determined measurement body part and the pre-stored examinee's basic body information (for example, age, gender, height, and weight) in operation 708.

Thereafter, the controller 280 may determine whether an analysis result identification signal is input in operation 710 and, when the analysis result identification signal is input, display a result of the analyzed body composition on a screen of the display unit 250 in operation 712.

When an analysis result identification end signal is input in operation 710, the controller 280 may proceed to operation 714 without displaying the analysis result. Further, the controller 280 may omit operation 710 and proceed to operation 712 to directly display the result of the analyzed body composition of the corresponding measurement body part on the screen.

After operation 712, when an analysis result display end signal is input, the controller 280 may determine whether an analysis result storage signal is input in operation 714. When the analysis result storage signal is input in operation 714, the controller 280 stores the body composition analysis result of the determined measurement body part in the storage unit 240 in operation 716.

When an analysis result storage end signal is input in operation 714, the controller 280 may proceed to operation 718 to determine whether a continuous measurement signal is input without storing the body composition analysis result of the corresponding measurement part. When the continuous measurement signal is input in operation 718, the controller 280 may return to operation 706 and repeatedly perform the following operations. In this case, the controller 280 may set the reference position and the reference body part as the previously determined measurement position (for example, a first measurement position) and measurement body part to determine the next measurement body part (for example, measurement body part corresponding to a second measurement position).

When a measurement end signal is input in operation 718, the controller 280 may end the body composition measurement. Meanwhile, when the measurement end signal is input in operation 704, the controller 280 may end the body composition measurement as well.

FIGS. 8A, 8B, 8C, 8D, 8E, and 8F illustrate user interface (UI) screens when a body composition is measured according to an embodiment of the present disclosure.

Figure 8A:
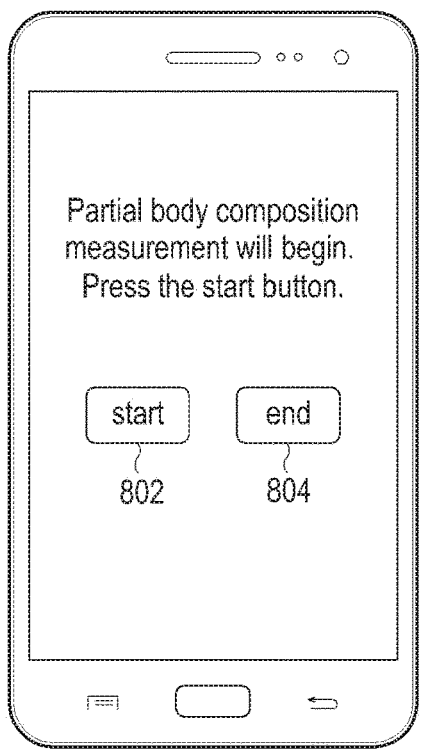
FIGS. 8A, 8B, 8C, 8D, 8E, and 8F illustrate user interface (UI) screens when a body composition is measured according to an embodiment of the present disclosure.

Referring to FIG. 8A, when an application for body composition measurement is executed, the controller 280 may display a start button 802 and an end button 804 along with a message that informs of the start of the body composition measurement on the screen of the display 250. When the user or the examinee presses the start button 802, a measurement start signal is generated and transmitted to the controller 280. When the user or examinee presses the end button 804, a measurement end signal is generated and transmitted to the controller 280, and the controller 280 ends the body composition measurement.

Figure 8B:
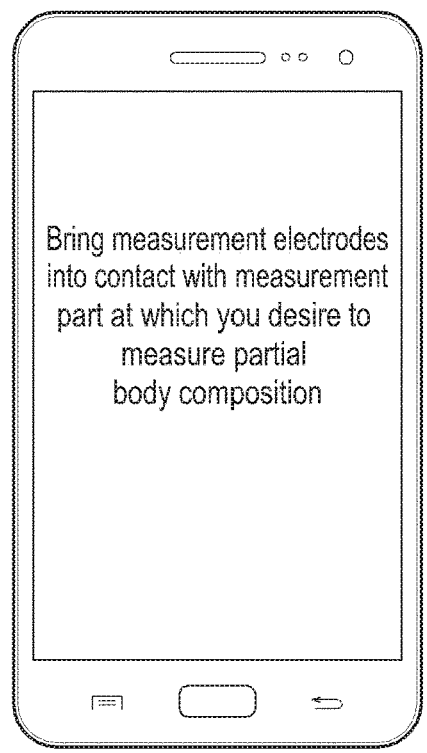

Referring to FIG. 8B, the controller 280 having received the measurement start signal may display, on the screen, a message that instructs the user to bring the measurement electrodes (for example, A, B, C, and D) (see FIG. 4B) into contact with the examinee's measurement body part of which the body composition is to be measured. The user or the examinee brings the measurement electrodes A, B, C, and D of the electronic device 200 into contact with the examinee's measurement body part of which the body composition is to be measured according to the notification message.

Figure 8C:
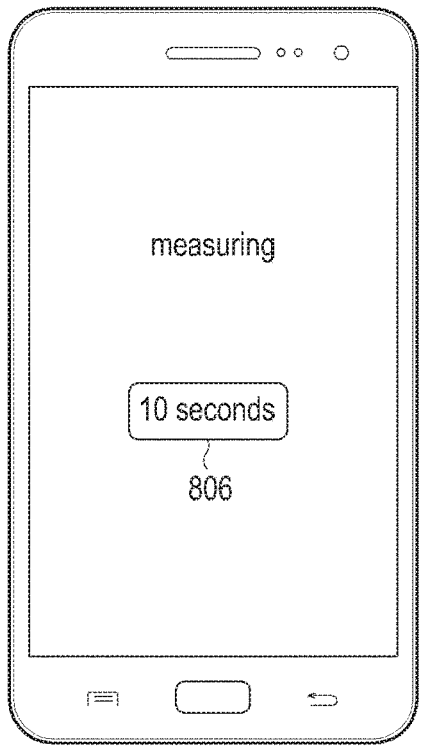

Referring to FIG. 8C, when the user or examinee brings the measurement electrodes A, B, C, and D into contact with a examinee's certain measurement body part according to the notification message, the controller 280 may display a preset measurement setting time 806 along with a message, which informs that the body composition is being measured, on the screen. Although the measurement setting time 806 is displayed to be counted down by a number for the measurement setting time (for example, 10 seconds) in FIG. 8C, the present disclosure is not limited thereto and the measurement setting time 806 may be displayed through various methods by which the counting down of the measurement time can be visually recognized through a decrease in a graphic-based object, such as a bar graph.

Figure 8D:
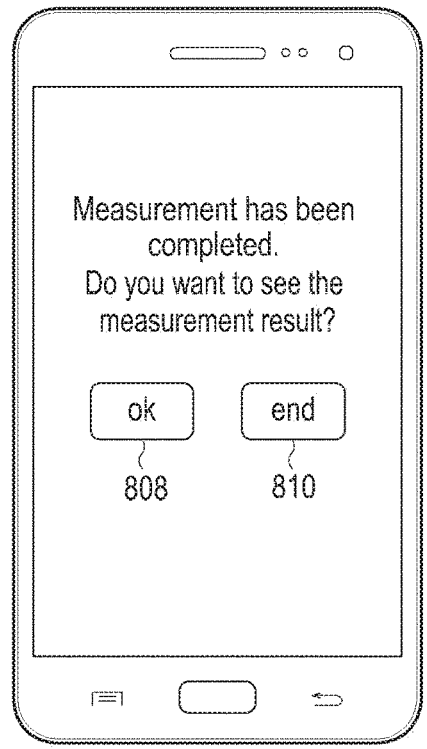

Referring to FIG. 8D, when the measurement is completed for the measurement setting time 806, the controller 280 may analyze the body composition of the corresponding measurement part and display an ok button 808 and an end button 810 along with a message, which inquires about whether to identify a result of the analysis on the screen. When the user presses the ok button 808, an analysis result identification signal is generated and transmitted to the controller 280, and the controller 280 displays an analysis result of the body composition of the corresponding measurement body part on the display (see FIGS. 11A, 11B, and 11C, and FIG. 12). When the user or the examinee presses the end button 810, an analysis result identification end signal is generated and transmitted to the controller 280.

Figure 8E:
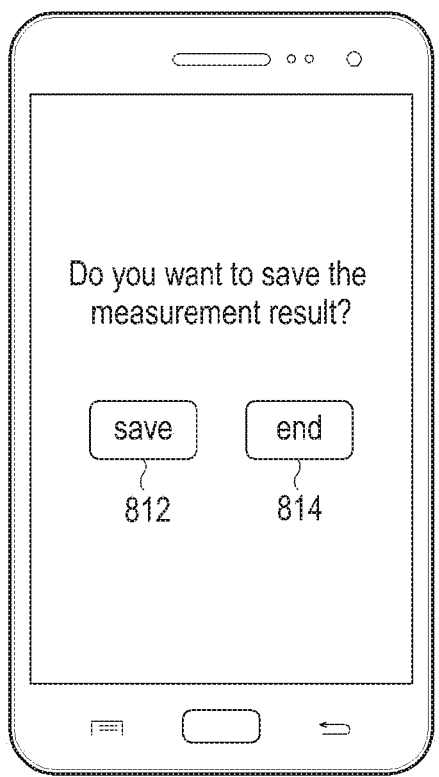

Referring to FIG. 8E, the controller 280 having received the identification end signal may display a save button 812 and an end button 814 along with a message, which inquires about whether to store the analyzed body composition result on the screen. When the user or the examinee presses the save button 812, an analysis result storage signal is generated and transmitted to the controller 280, and the controller 280 may store the analysis result of the body composition of the corresponding measurement part in the storage unit 240. When the user or the examinee presses the end button 814, an analysis result storage end signal is generated and transmitted to the controller 280.

Figure 8F:
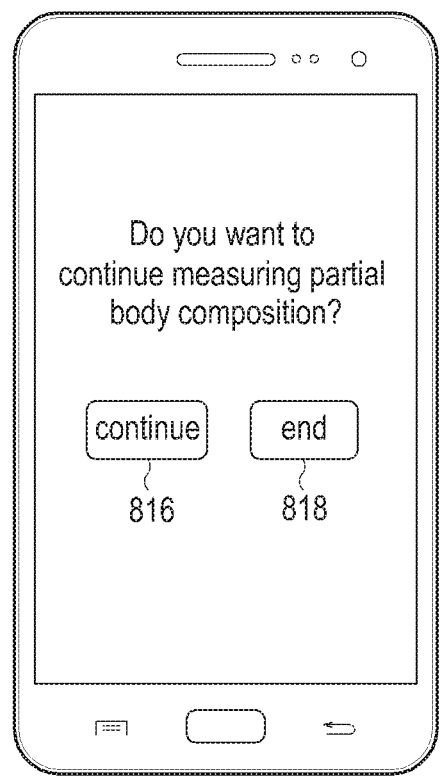

Referring to FIG. 8F, the controller 280 having received the analysis result storage end signal may display a continue button 816 and an end button 818 along with a message, which inquires about whether to continue to measure the body composition on the screen without storing the analyzed body composition result. When the user or the examinee presses the continue button 816, a continuous measurement signal may be generated and transmitted to the controller 280, and the controller 280 may return to operation 706 of FIG. 7 to determine the next measurement body part and measure body composition. When the user or examinee presses the end button 818, a measurement end signal is generated and transmitted to the controller 280, and the controller 280 ends the body composition measurement.

Figure 9:
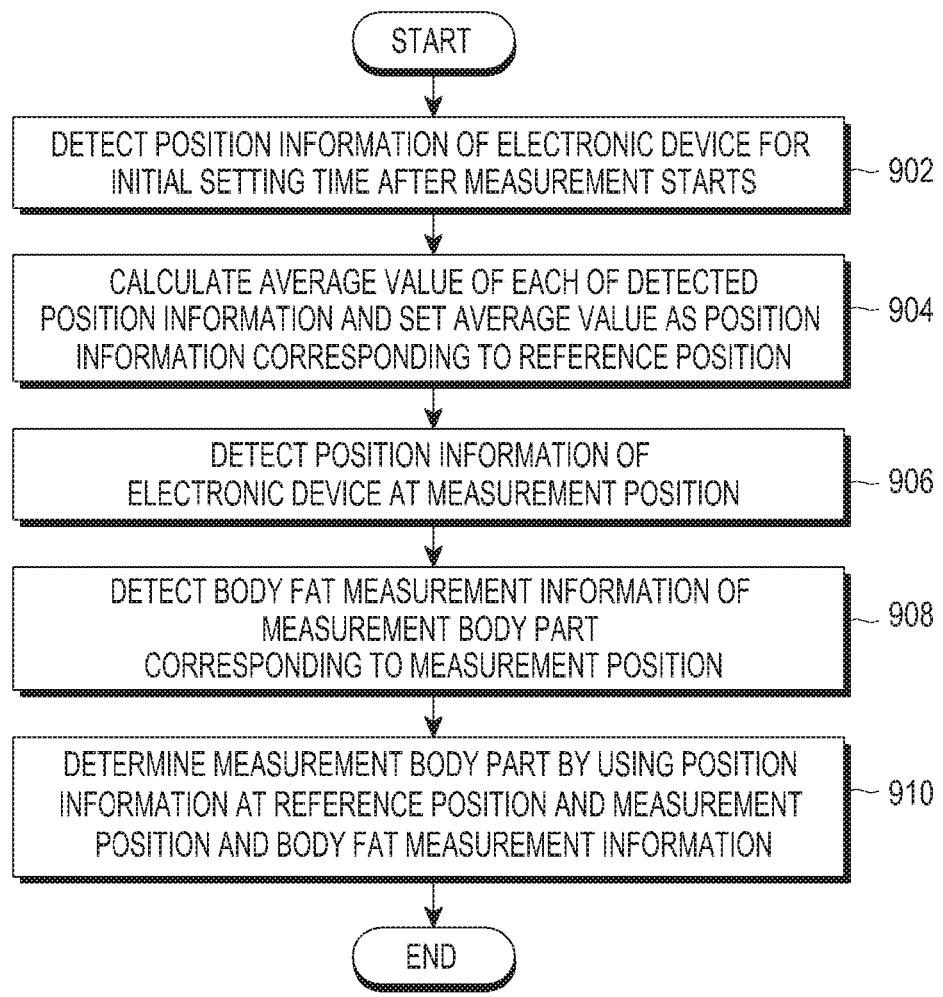
FIG. 9 is a flowchart illustrating a method of measuring body composition by an electronic device which can automatically recognize a measurement body part according to an embodiment of the present disclosure.

FIG. 9 is a flowchart illustrating a method of measuring body composition by an electronic device which can automatically recognize a measurement body part according to an embodiment of the present disclosure. More specifically, FIG. 9 is a flowchart for describing operation 706 of FIG. 7.

Referring to FIG. 9, in operation 902, the measurement position determination module 602 of the controller 280 detects position information of the electronic device 200 through the position sensor unit 210 for an initial setting time (for example, about 1 second) after the measurement starts. The position information may include, for example, at least one of an acceleration value detected by the acceleration sensor 302, a geomagnetic value detected by the geomagnetic sensor 304, and an altitude value detected by the altitude sensor 306.

The measurement position determination module 602 of the controller 280 may calculate an average value of the position information detected by the position sensor unit 210 for the initial setting time and set the average value as position information of the electronic device 200 corresponding to a reference position in operation 904. For example, the measurement position determination module 602 may set the calculated average acceleration value, average geomagnetic value, and average altitude value as reference values corresponding to the position information of the electronic device 200 at the reference position. At this time, a reference body part corresponding to the reference position may be preset by default. For example, when the reference body part is preset as the abdomen by default, it is assumed that the user places the electronic device 200 on the examinee's abdomen for the body composition measurement and starts the body composition measurement. In the body composition measurement, the measurement position determination module 602 may determine the reference body part corresponding to the reference position as the examinee's abdomen and determine a position of the electronic device 200 corresponding to the abdomen as the reference position.

The reference body part corresponding to the reference position may be preset by the user or the examinee. For example, the user or the examinee may preset the reference body part corresponding to the reference position by inputting a voice through the input unit 230, such as a microphone, a keypad, and a touch pad or selecting a measurement body part displayed on the display unit 250 before the body composition measurement. It is assumed that the preset reference body part corresponding to the reference position is the examinee's abdomen in an embodiment of the present disclosure.

After setting the position information of the electronic device 200 corresponding to the reference position in operation 904, the measurement position determination module 602 of the controller 280 detects position information of the electronic device 200 at the measurement position corresponding to the measurement body part which the examinee desires to measure through the position sensor unit 210 in operation 906.

The measurement part determination module 604 of the controller 280 detects body fat measurement information at the measurement position through the partial body fat measurement unit 220 in operation 908. The body fat measurement information may include, for example, at least one of an impedance value and a skin conductivity value detected by the body resistance measurement module 502 and a subcutaneous fat thickness detected by the subcutaneous fat measurement module 504.

The measurement part determination module 604 of the controller 280 may determine the measurement body part corresponding to the measurement position based on the body fat measurement information detected at the measurement position and the position and the attitude of the electronic device 200 at the measurement position moved to from the reference position determined by the measurement position determination module 602 in operation 910.

Figure 10:
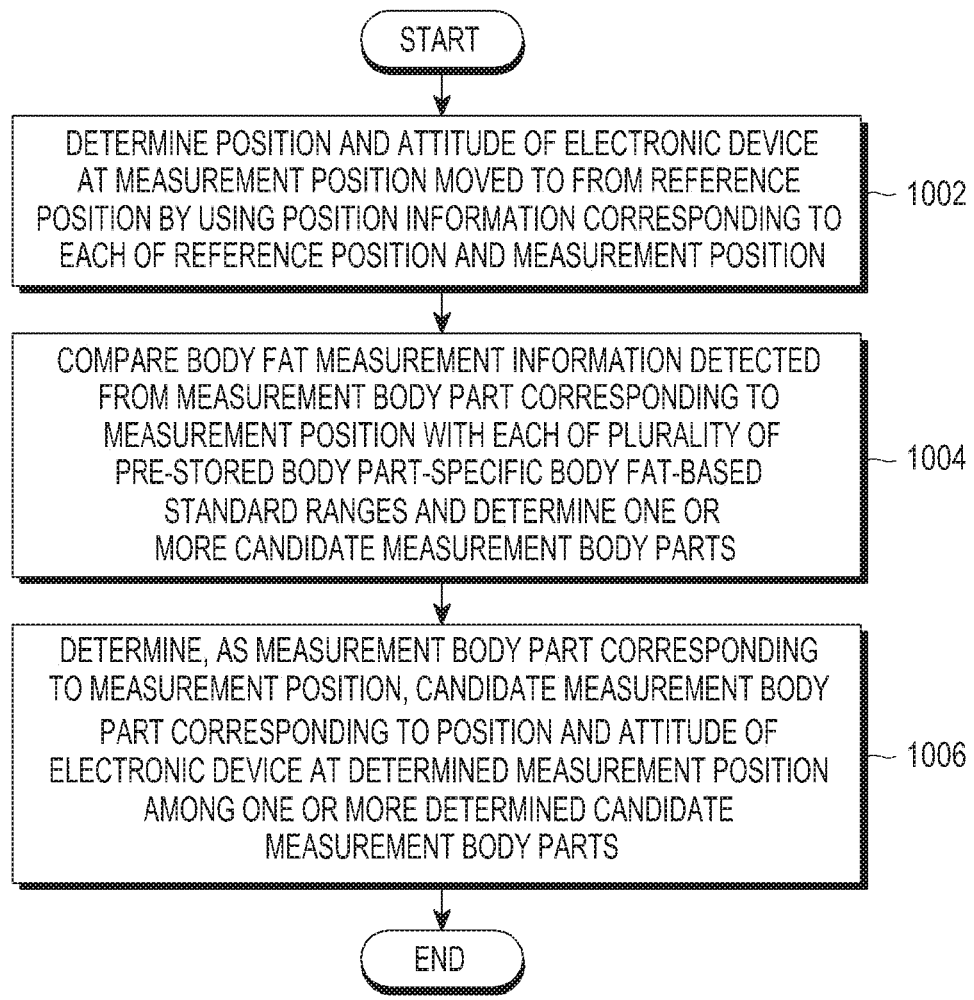
FIG. 10 is a flowchart illustrating a method of measuring body composition by an electronic device which can automatically recognize a measurement body part according to an embodiment of the present disclosure.

FIG. 10 is a flowchart illustrating a method of measuring body composition by an electronic device which can automatically recognize a measurement body part according to an embodiment of the present disclosure. More specifically, FIG. 10 is a flowchart for describing operation 910 of FIG. 9.

Referring to FIG. 10, the controller 280 determines a position and an attitude of the electronic device 200 at the measurement position moved to from the reference position based on the position information of the electronic device 200 corresponding to the reference position and the position information of the electronic device 200 corresponding to the measurement position through the measurement position determination module 602 in operation 1002.

Operation 1002 may include a process of determining, by the measurement position determination module 602, a movement speed, a movement distance, and a movement direction of the electronic device 200 at the measurement position moved to from the reference position by using an average acceleration value of the electronic device 200 at the reference position and an acceleration value of the electronic device 200 at the measurement position, detected by the position sensor unit 210.

Operation 1002 may include a process of determining, by the measurement position determination module 602, an attitude angle at the measurement position moved to from the reference position by using an average geomagnetic value of the electronic device 200 at the reference position and a geomagnetic value of the electronic device 200 at the measurement position, detected by the position sensor unit 210.

Operation 1002 may include a process of determining, by the measurement position determination module 602, an altitude at the measurement position moved to from the reference position by using an average altitude value of the electronic device 200 at the reference position and an altitude value of the electronic device 200 at the measurement position, detected by the position sensor unit 210.

Operation 1002 may include a process of determining, by the measurement position determination module 602, the position and the attitude of the electronic device 200 at the measurement position based on at least one of the movement distance, the movement direction, the attitude angle, and the altitude of the electronic device 200 at the determined measurement position.

Through the measurement part determination module 604, the controller 280 may compare the body fat measurement information detected from the measurement body part corresponding to the measurement position with each of a plurality of pre-stored body part-specific body fat-based standard ranges and determine, as at least one candidate measurement body part at the measurement position, at least one measurement body part having the detected body fat measurement information, which is included in the plurality of pre-stored body part-specific body fat-based standard ranges in common among a plurality of preset body parts.

Operation 1004 may include a process of, by the measurement part determination module 604, comparing an impedance value of the plurality of detected body fat measurement information with a body part-specific impedance standard range among the plurality of pre-stored body part-specific body fat-based standard ranges and selecting at least one first measurement body part having the detected impedance value, which corresponds to the pre-stored body part-specific impedance standard range, among the plurality of preset body parts.

Operation 1004 may include a process of, by the measurement part determination module 604, comparing a subcutaneous fat thickness of the plurality of detected body fat measurement information with a body part-specific subcutaneous fat thickness standard range among the plurality of pre-stored body part-specific body fat-based standard ranges and selecting at least one second measurement body part having the detected subcutaneous fat thickness, which corresponds to the pre-stored body part-specific subcutaneous fat thickness standard range, among the plurality of preset body parts.

Operation 1004 may include a process of, by the measurement part determination module 604, comparing a skin conductivity value of the plurality of detected body fat measurement information with a body part-specific skin conductivity standard range among the plurality of pre-stored body part-specific body fat-based standard ranges and selecting at least one third measurement body part having the detected skin conductivity value, which corresponds to the pre-stored body part-specific skin conductivity standard range, among the plurality of preset body parts.

Operation 1004 may include a process of determining at least one measurement body part included in at least one of the first to third measurement body parts in common as at least one candidate measurement body part corresponding to the measurement position by the measurement part determination module 604.

Thereafter, the controller 280 may determine, as the measurement body part corresponding to the measurement position, the candidate measurement body part corresponding to the position and the attitude of the electronic device 200 at the measurement position determined by the measurement position determination module 602 among at least one candidate measurement body part determined by the measurement part determination module 604 in operation 1006.

Operation 1006 may include a process of determining, by the measurement part determination module 604, a left and right movement position of the electronic device 200 at the measurement position from the reference position through the movement speed, the movement distance, and the movement direction of the electronic device 200 from the reference position to the measurement position, determined by the measurement position determination module 602.

Operation 1006 may include a process of determining, by the measurement part determination module 604, an up and down movement position of the electronic device 200 at the measurement position from the reference position through the altitude of the electronic device 200 at the measurement position determined by the measurement position determination module 602.

Operation 1006 may include a process of determining, by the measurement part determination module 604, a front and back movement position of the electronic device 200 at the measurement position from the reference position through the attitude of the electronic device 200 at the measurement position determined by the measurement position determination module 602.

Operation 1006 may include a process of, by the measurement determination module 604, finally determining, as the measurement body part at the measurement position, the candidate measurement body part corresponding to the left and right movement position, the up and down movement position, and the front and back movement position at the measurement position moved to from the reference position determined by the measurement position determination module 602 among at least one determined candidate measurement body part. Accordingly, the controller 280 may automatically recognize the measurement body part of the examinee corresponding to measurement position.

Figure 11A:
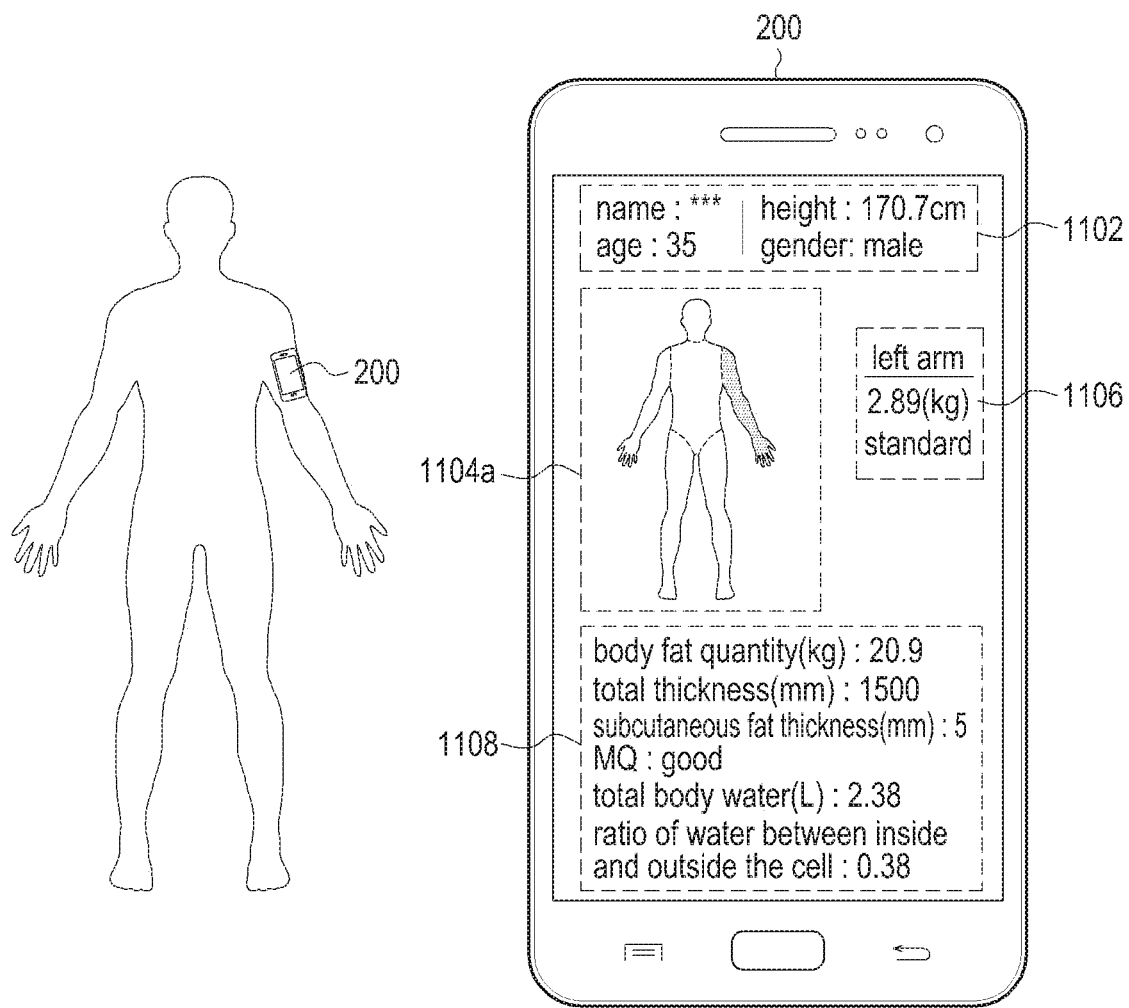
FIGS. 11A, 11B, and 11C illustrate a UI screen that shows a partial body composition analysis result according to an embodiment of the present disclosure.
Figure 11B:
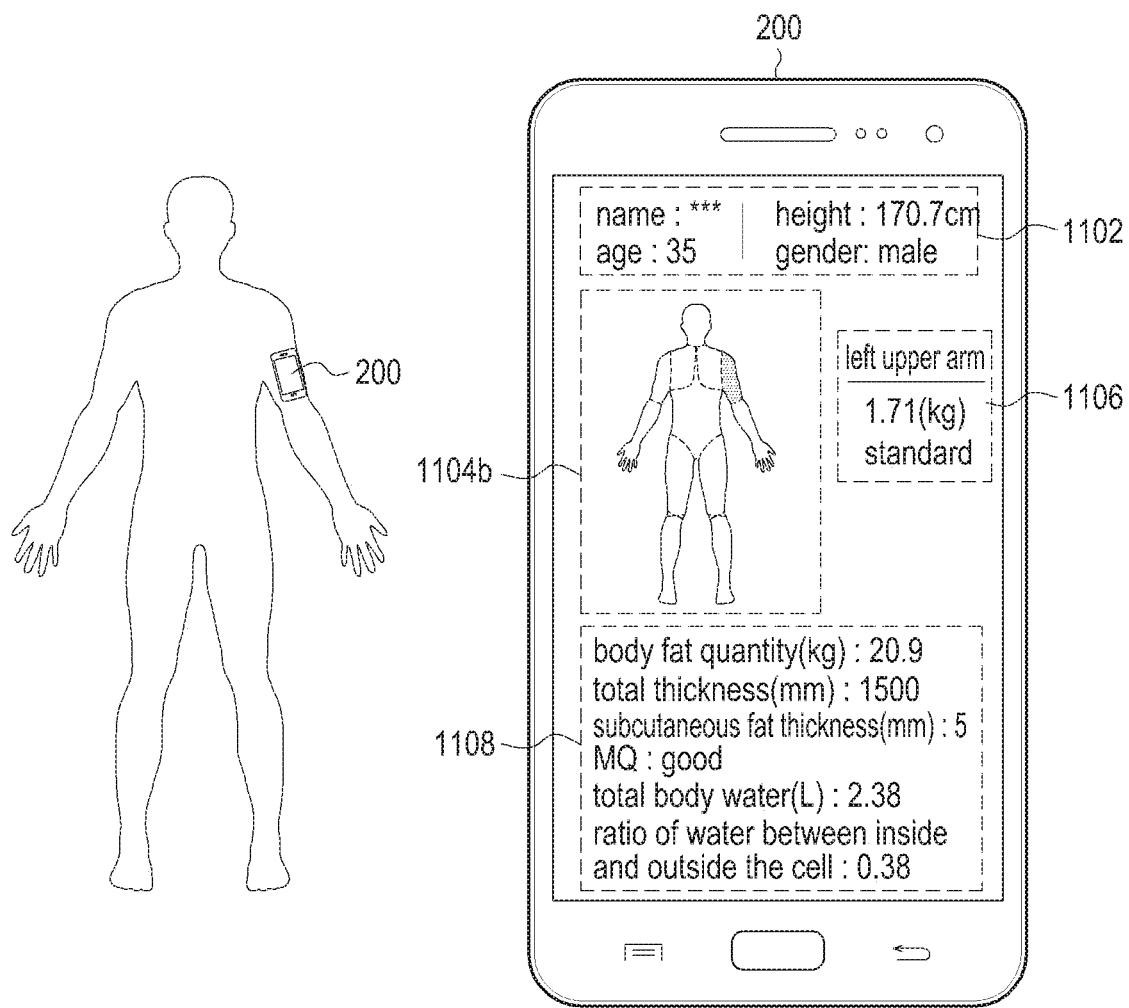
Figure 11C:
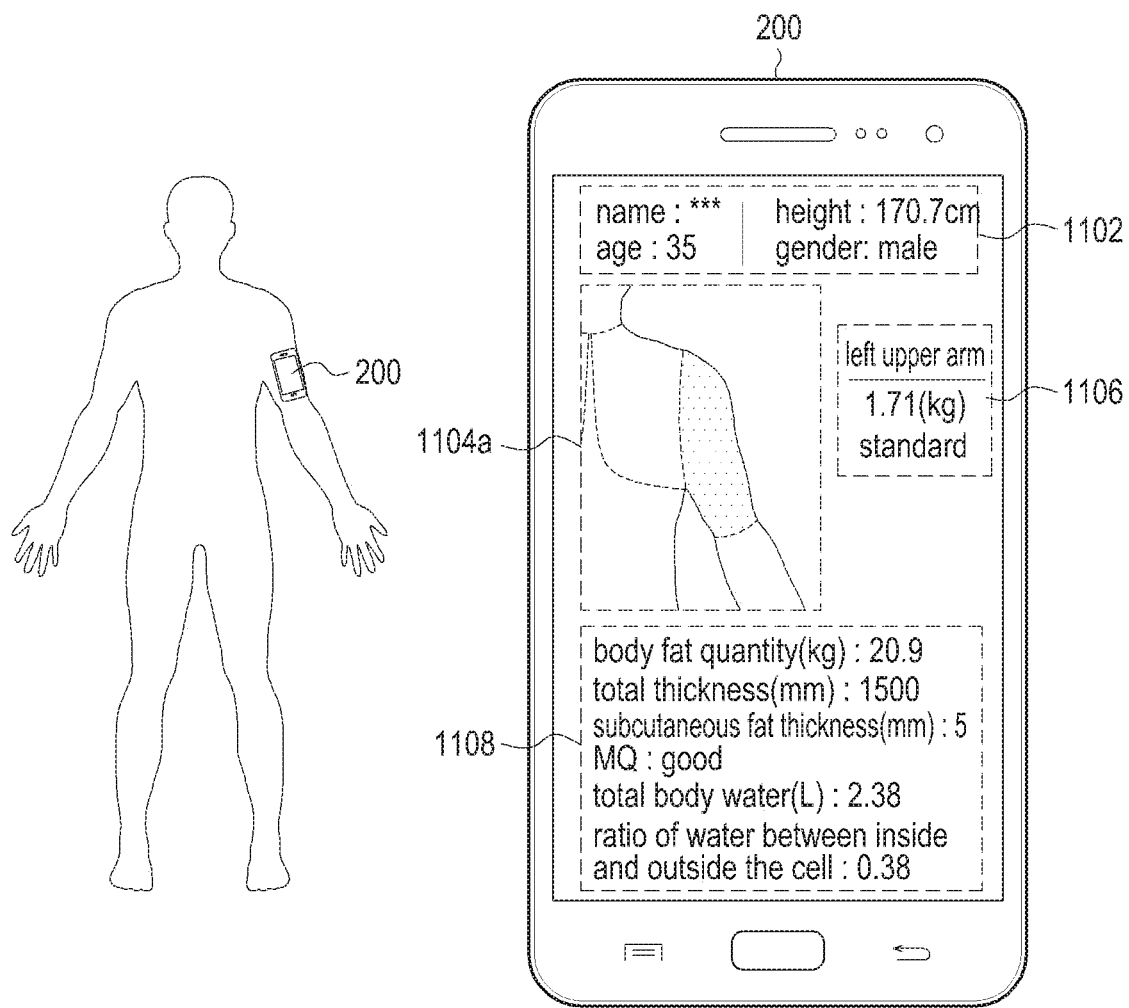

FIGS. 11A, 11B, and 11C illustrate a UI screen that shows a partial body composition analysis result according to an embodiment of the present disclosure.

Referring to FIG. 11A, the controller 280 may display the body composition analysis result of the determined measurement body part of the examinee on the screen of the display unit 250. A basic information display area 1102 for displaying examinee's basic information, a measurement body part display area 1104a for displaying a determined measurement body part, a measurement information display area 1106 for displaying measurement information of the measurement body part, and a body composition display area 1108 for displaying a body composition analysis result of the measurement body part may be included on the screen.

The basic information display area 1102 may display examinee's basic information, such as a name (or identification (ID)), age, gender, height, and weight of the examinee. The measurement body part display area 1104a may correspond to an area displayed to allow the user or the examinee to visually recognize the determined measurement body part (for example, left arm (LA)) according to an embodiment of the present disclosure and may be displayed in various forms including at least one of graphics, text, and color. For example, the measurement body part display area 1104a may display a human body modeling drawing classified into body parts such that a part corresponding to the determined measurement body part is distinguished with a color or the part is displayed in a graphic form to allow the user or the examinee to easily recognize the determined measurement body part through an action, such as flicker. In this case, the user may intuitively recognize the determined measurement body part.

The measurement information display area 1106 may correspond to an area showing measurement information of the determined measurement body part according to an embodiment of the present disclosure and may display a name, muscle quantity (Kg), and obesity level of the corresponding measurement body part.

The body composition display area 1108 corresponds to an area for displaying a body composition analysis result of the determined measurement body part. The body composition display area 1108 may display a total thickness (mm), subcutaneous fat thickness (mm), muscle quality (MQ), body water (L), and ratio of water between inside and outside the cell of the determined measurement body part.

Display items of the measurement information display area 1106 and the body composition display area 1108 may be shared therebetween. For example, the measurement information display area 1106 may include at least some of the display items of the body composition display area 1108.

Referring to FIG. 11B, it is noted that the measurement body part display area 1104b displays the examinee's measurement body parts, which are further subdivided than those displayed in the measurement body part display area 1104a of FIG. 11A. The controller 280 may display a plurality of preset body parts in the measurement body part display area 1104a or 1104b according to settings. The settings of the plurality of preset body parts can be changed by the user or the examinee before the body composition measurement. As the measurement body parts are further subdivided, partial body composition can be measured more accurately.

Referring to FIG. 11C, the measurement body part display area 1104c may display an enlarged measurement body part of the examinee determined by the controller 280 or display an enlarged measurement body part selected by the user or the examinee.

Figure 12:
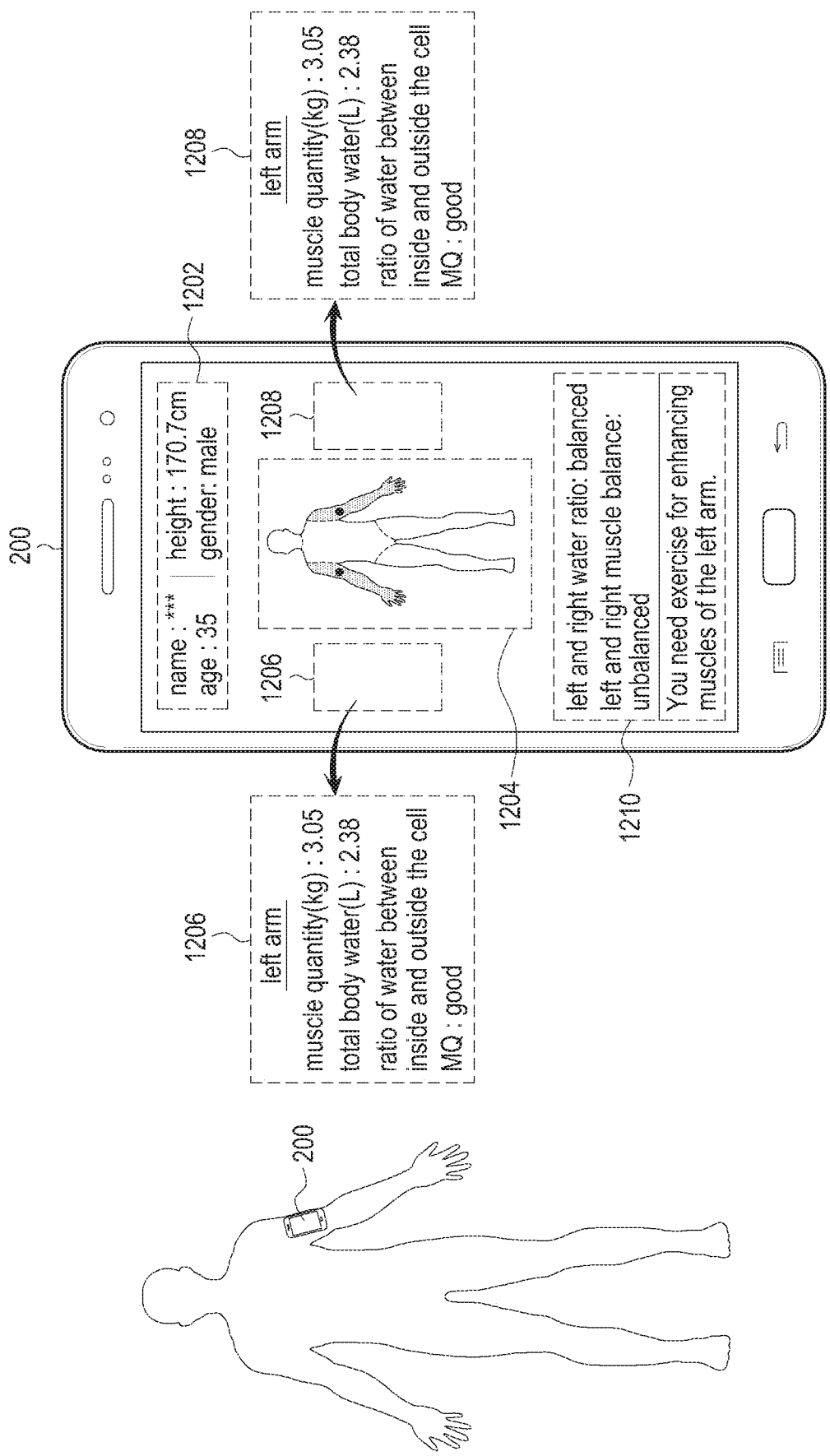
FIG. 12 illustrates a UI screen that shows a combined body composition analysis result according to an embodiment of the present disclosure.

FIG. 12 illustrates a UI screen that shows a combined body composition analysis result according to an embodiment of the present disclosure.

Referring to FIG. 12, the controller 280 may also display a combined body composition analysis result of at least one determined measurement body part of the examinee on the screen of the display unit 250. A basic information display area 1202 for displaying examinee's basic information, a measurement body part display area 1204 for displaying a determined measurement body part, measurement information display areas 1206 and 1208 for display measurement information and/or a body composition analysis result of the determined measurement body part, and a diagnosis result display area 1210 for displaying a comprehensive diagnosis of at least one measurement body part or a specialist's advice based on the measurement information and/or the body composition analysis result of the measurement body part may be included on the screen.

Descriptions for the basic information display area 1202, the measurement body part display area 1204, and the measurement information display areas 1206 and 1208 are the same as those in FIGS. 11A, 11B, and 11C. However, the measurement information display areas 1206 and 1208 may display a combination of the display items of the body composition display areas 1106 of FIGS. 11A, 11B, and 11C.

The diagnosis result display area 1210 may display a diagnosis result, such as left and right balance and top and bottom balance of the muscle and the ratio of water between inside or outside the body based on the measurement information and/or the body composition analysis result of at least one determined measurement body part, and a specialist's advice based on the diagnosis result. For example, when the measurement information and/or the body composition analysis results for the left arm and the right arm are displayed on the measurement information display areas 1206 and 1208, respectively, the diagnosis result display area 1210 may display a diagnosis result of left and right muscle balance for the left and right arms (for example, "left and right muscle balance: unbalanced") or a diagnosis result of left and right water ratio for the left and right arms (for example, "left and right water ratio: balanced"). Further, the diagnosis result display area 1210 may also display a specialist's advice on the diagnosis result (for example, "You need exercise for enhancing muscle of the left arm").

Figure 13:
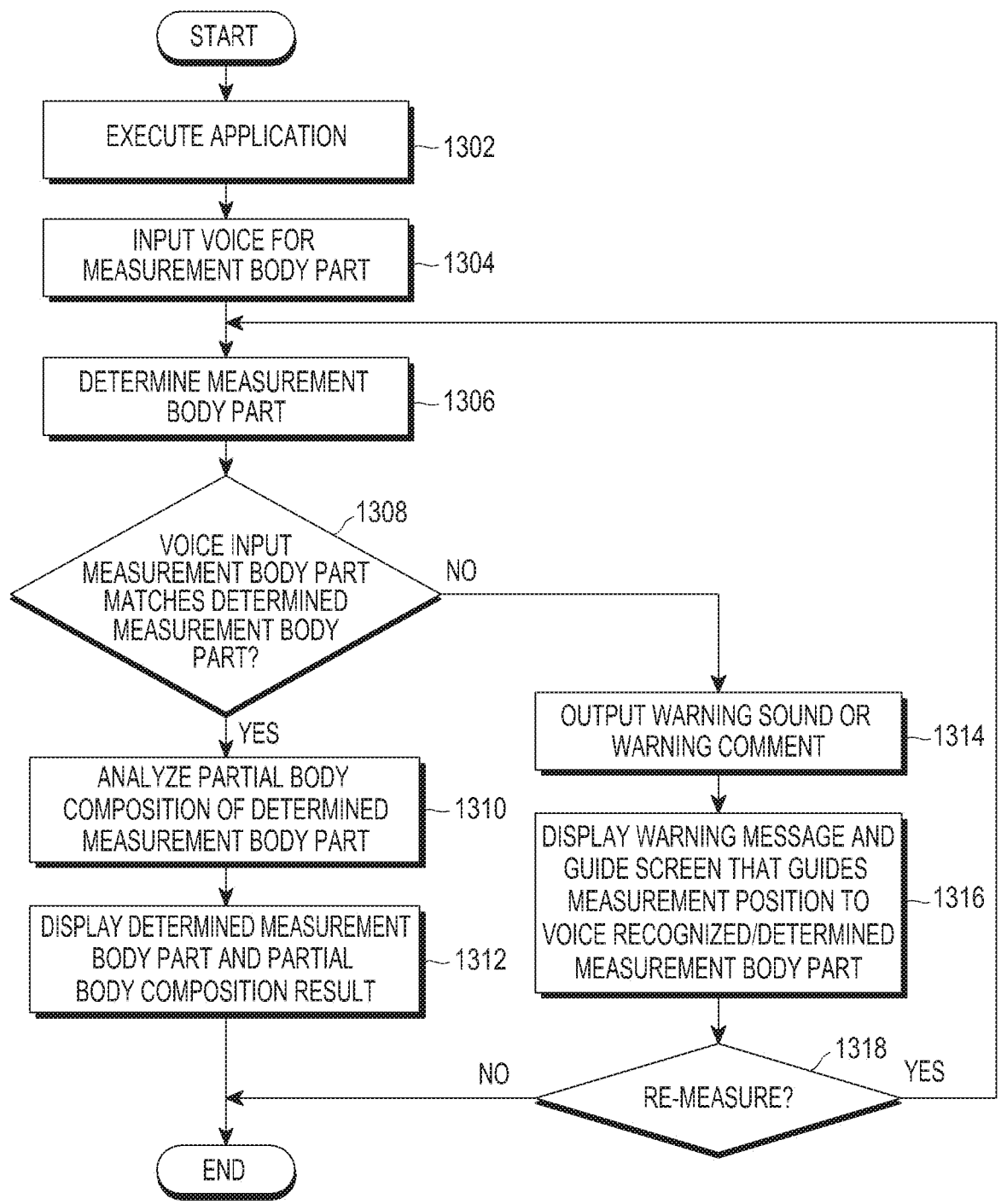
FIG. 13 is a flowchart illustrating a method of measuring body composition by an electronic device which can automatically recognize a measurement body part based on a voice input scheme according to an embodiment of the present disclosure.

FIG. 13 is a flowchart illustrating a method of measuring body composition by an electronic device which can automatically recognize a measurement body part based on a voice input scheme according to an embodiment of the present disclosure.

Referring to FIG. 13, an application for measuring body composition is executed in operation 1302. When the application is executed, the controller 280 may receive an input of a voice for a measurement body part through the input unit 230, such as a microphone and recognize the corresponding measurement body part in operation 1304. After the voice input, when the user or the examinee brings the measurement electrodes A, B, C, and D (see FIG. 4B) of the electronic device 200 into contact with the measurement body part of the examinee, the controller 280 may determine the measurement body part corresponding to the contacted measurement body part as described in FIGS. 7, 9, and 10 in operation 1306. Thereafter, the controller 280 may determine whether the voice recognized measurement body part matches the determined measurement body part in operation 1308. When the voice recognized measurement body part matches the determined measurement body part in operation 1308, the controller 280 may analyze a body composition of the determined measurement body part by using body fat measurement information detected from the determined measurement body part, which has been described in operation 708 of FIG. 7, in operation 1310 and display the determined measurement body part and a result of the analyzed body composition in operation 1312.

Meanwhile, when the voice recognized measurement body part does not match the determined measurement body part in operation 1308, the controller 280 may output at least one of a warning sound and a warning comment that informs the user or the examinee that the measurement position of the electronic device 200 is incorrect through the sound output unit 260 in operation 1314. Further, the controller 280 may display a guide screen that guides the measurement body part to induce the user or the examinee to accurately place the measurement electrodes (for example, A, B, C, and D) (see FIG. 4B) of the electronic device 200 at the position corresponding to the measurement body part recognized through the voice input by displaying at least one of the warning message and the voice recognized or the determined measurement body part on the screen of the display unit 250 in operation 1316. The controller 280 may determine whether a re-measurement signal for re-measuring the body composition is input in operation 1318. When the re-measurement signal is input, the controller 280 may return to operation 1306 in which the electronic device 200 is moved by the user and repeatedly perform the following operations to measure the body composition of the measurement body part corresponding to the contacted part, which the measurement electrodes A, B, C, and D of the electronic device 200 contact. When a re-measurement end signal is input in operation 1318, the controller 280 may end the body composition measurement.

Figure 14A:
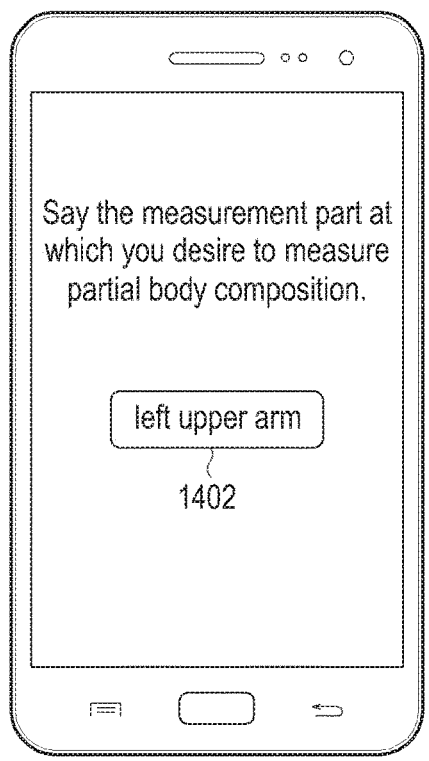
FIGS. 14A, 14B, and 14C illustrate UI screens when body composition is measured according to a voice input scheme illustrated in FIG. 13 according to an embodiment of the present disclosure.
Figure 14B:
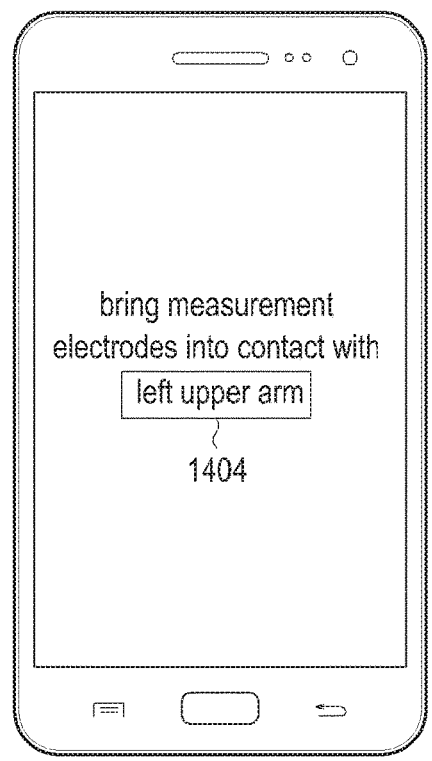
Figure 14C:
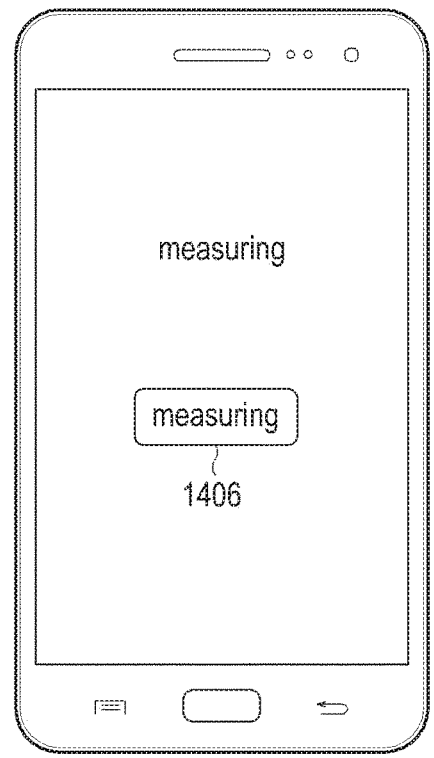

FIGS. 14A, 14B, and 14C illustrate UI screens when body composition is measured according to the voice input scheme illustrated in FIG. 13 according to an embodiment of the present disclosure.

Referring to FIG. 14A, when an application for body composition measurement is executed, the controller 280 may display both a notification message for receiving a voice for a measurement body part from which the user desires to measure body composition and a voice recognition display field 1402 by which the user can visually recognize the voice recognized measurement body part on the screen of the display unit 250. For example, when the user or the examinee makes a voice input of a left upper arm part, the controller 280 may recognize the voice input and display the corresponding measurement body part on the screen. Although FIG. 14A illustrates the voice recognized measurement body part in a text form, the present disclosure is not limited thereto and the voice recognized measurement body part may be displayed in a graphic form in a human body model classified into preset body parts.

Referring to FIG. 14B, the controller 280 may display a notification message that induces the user or the examinee to bring the measurement electrodes A, B, C, and D (see FIG. 4B) of the electronic device 200 into contact with the recognized measurement body part, the notification message including a voice recognition display field 1404 for displaying the voice recognized measurement body part. The user or the examinee may bring the measurement electrodes A, B, C, and D of the electronic device 200 into contact with the corresponding measurement body part of the examinee according to the notification message.

Referring to FIG. 14C, when the user or the examinee brings the measurement electrodes A, B, C, and D of the electronic device 200 into contact with a certain measurement body part of the examinee, the controller 280 may determine the contacted measurement body part, measure body composition of the determined measurement body part, and display both a notification message, which informs that the body composition of the determined measurement body part is being measured, and a measurement setting time display field 1406 for displaying a measurement setting time (for example, about 10 seconds).

Figure 15:
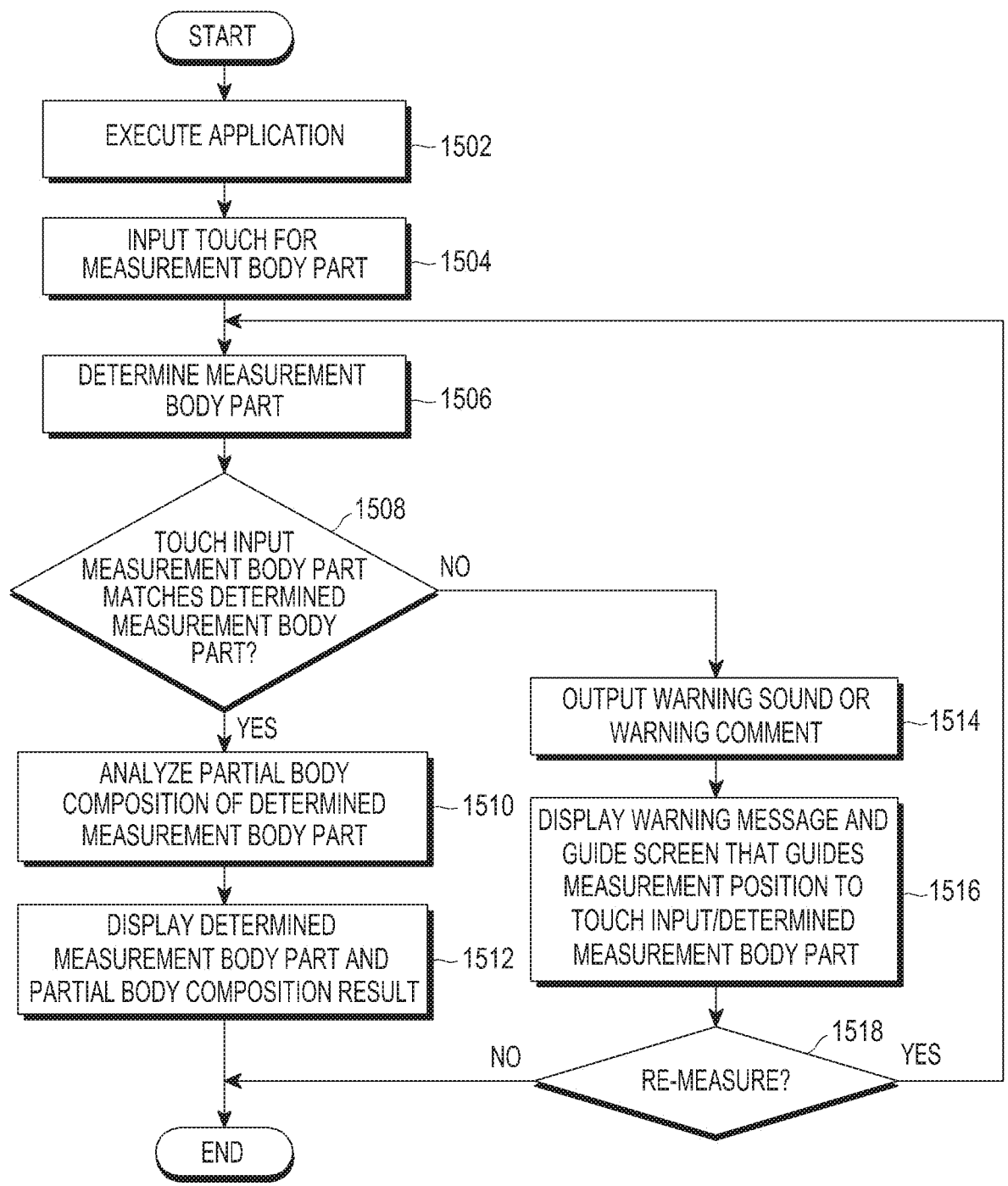
FIG. 15 is a flowchart illustrating a method of measuring body composition by an electronic device which can automatically recognize a measurement body part based on a touch input scheme according to an embodiment of the present disclosure.

FIG. 15 is a flowchart illustrating a method of measuring body composition by an electronic device which can automatically recognize a measurement body part based on a touch input scheme according to an embodiment of the present disclosure.

Referring to FIG. 15, an application for measuring body composition is executed in operation 1502. When the application is executed, the controller 280 may receive an input of a touch for a measurement body part selected by the user or the examinee through the input unit 230, such as a plurality of selection buttons 1602a and 1602b (see FIGS. 16A and 16B) for selecting the measurement body part at which the user or examinee desires to measure partial body composition on the screen of the display unit 250 and recognize the corresponding measurement body part in operation 1504. When the user or the examinee brings the measurement electrodes A, B, C, and D (see FIG. 4B) of the electronic device 200 into contact with the examinee's measurement body part after the touch input for the corresponding measurement body part (for example, abdomen) or while the touch input is maintained in a state where the selection button 1602a or 1602b corresponding to the corresponding measurement body part (for example, abdomen) is pressed, the controller 280 may determine the measurement body part corresponding to the contacted measurement body part as illustrated in FIGS. 7, 9, and 10 in operation 1506. Thereafter, the controller 280 determines whether the touch input measurement body part matches the determined measurement body part in operation 1508. When the touch input measurement body part matches the determined measurement body part in operation 1508, the controller 280 may analyze a body composition of the determined measurement body part by using body fat measurement information detected from the determined measurement body part, which has been described in operation 708 of FIG. 7, in operation 1510 and display the determined measurement body part and a result of the analyzed body composition in operation 1512.

Meanwhile, when the touch input measurement body part does not match the determined measurement body part in operation 1508, the controller 280 may output at least one of a warning sound and a warning comment that informs the user or the examinee that the measurement position of the electronic device 200 is incorrect through the sound output unit 260 in operation 1514. Further, the controller 280 may display a guide screen that guides the measurement body part to induce the user or the examinee to accurately place the measurement electrodes (for example, A, B, C, and D) (see FIG. 4B) of the electronic device 200 at the position corresponding to the measurement body part which the user or the examinee desires to measure by displaying at least one of the warning message and the touch input or the determined measurement body part on the screen of the display unit 250 in operation 1516. The controller 280 may determine whether a re-measurement signal for re-measuring the body composition is input in operation 1518. When the re-measurement signal is input, the controller 280 may return to operation 1506 in which the electronic device 200 is moved by the user and repeatedly perform the following operations to measure the body composition of the measurement body part corresponding to the contacted part, which the measurement electrodes A, B, C, and D of the electronic device 200 contact. When a re-measurement end signal is input in operation 1518, the controller 280 may end the body composition measurement.

FIGS. 16A, 16B, 16C, and 16D illustrate UI screens when body composition is measured according to the touch input scheme illustrated in FIG. 15 according to an embodiment of the present disclosure.

Figure 16A:
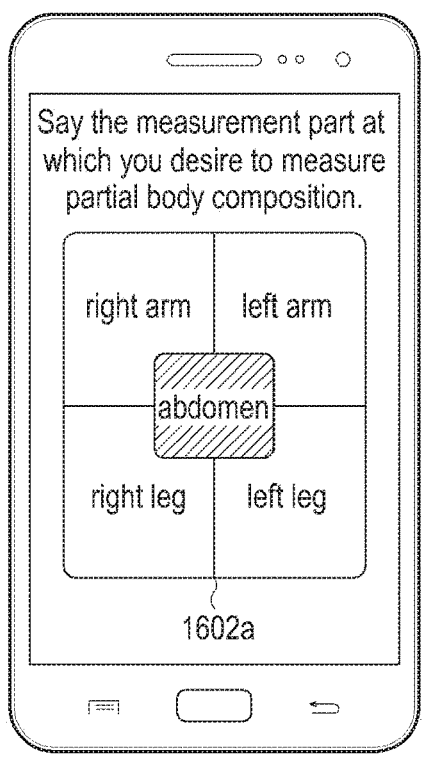
FIGS. 16A, 16B, 16C, and 16D illustrate UI screens when body composition is measured according to the touch input scheme illustrated in FIG. 15 according to an embodiment of the present disclosure.
Figure 16B:
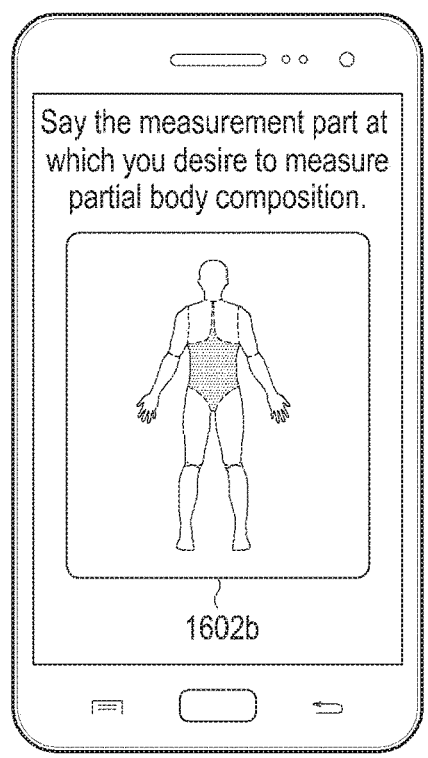

Referring to FIGS. 16A and 16B, when an application for body composition measurement is executed, the controller 280 may display both a notification message for receiving an input of a touch for a measurement body part from which the user or the examinee desires to measure body composition and a measurement part selection button 1602a or 1602b by which the user of the examinee can visually recognize a plurality of preset body parts. The measurement body part selection button may be displayed in a type 1602a in which the measurement body parts are displayed in a text form as illustrated in FIG. 16A or a type 1602b in which the measurement body parts are displayed in a graphic form by which the user or the examinee can more intuitively recognize the measurement body part as illustrated in FIG. 16B.

For example, when a left upper arm is selected by the user or the examinee through the measurement body part selection button 1602a or 1602b, the controller 280 may display the plurality of preset body parts on the screen in such a manner that the measurement body part selected from the plurality of the preset body parts is displayed with a color or an action, such as flicker so that the corresponding measurement body part can be visually recognized.

Figure 16C:
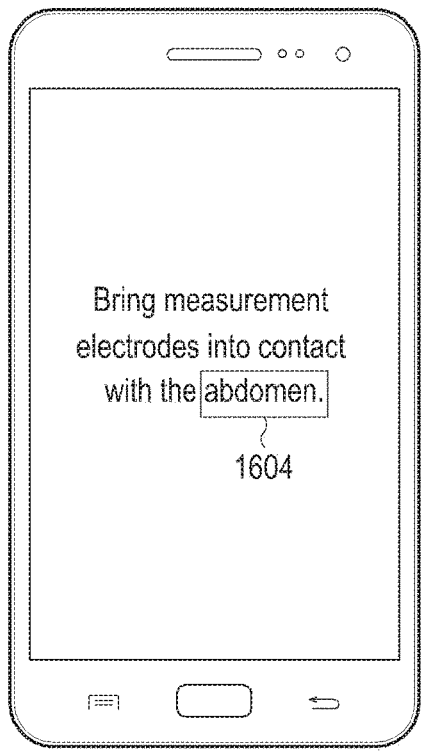

Referring to FIG. 16C, the controller 280 may display a notification message that induces the user or the examinee to bring the measurement electrodes A, B, C, and D (see FIG. 4B) of the electronic device 200 into contact with the recognized measurement body part, the notification message including a touch recognition display field 1604 for displaying the touch input measurement body part. The user or the examinee may bring the measurement electrodes A, B, C, and D of the electronic device 200 into contact with the corresponding measurement body part of the examinee according to the notification message.

Figure 16D:
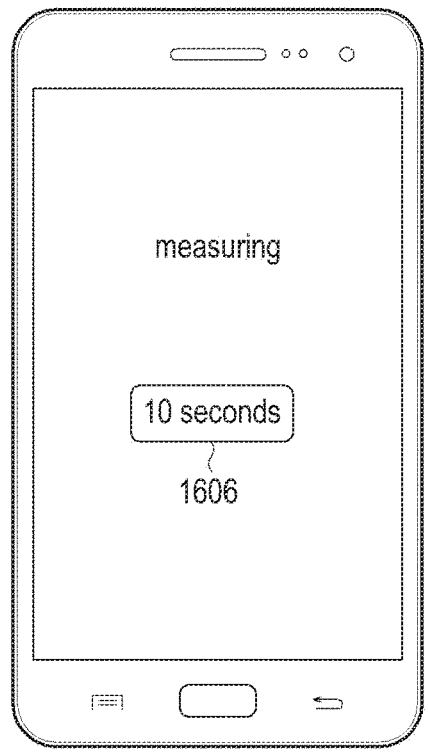

Referring to FIG. 16D, when the user or the examinee brings the measurement electrodes A, B, C, and D of the electronic device 200 into contact with a certain measurement body part of the examinee, the controller 280 may determine the contacted measurement body part, measure body composition of the determined measurement body part, and display both a notification message, which informs that the body composition of the determined measurement body part is being measured, and a measurement setting time display field 1606 for displaying a measurement setting time (for example, about 10 seconds).

Figure 17A:
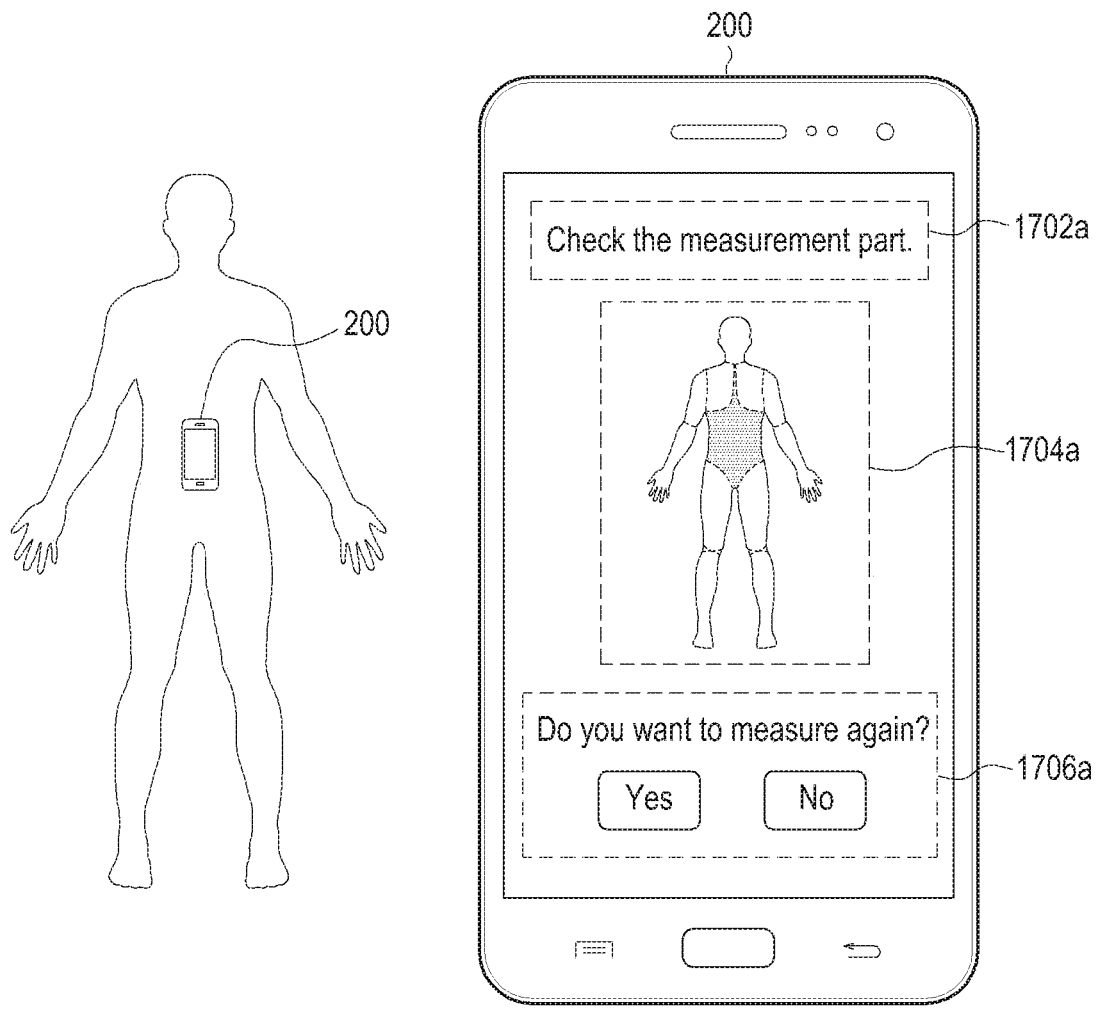
FIGS. 17A and 17B illustrate UI screens when body composition is measured according to an embodiment of the present disclosure.
Figure 17B:
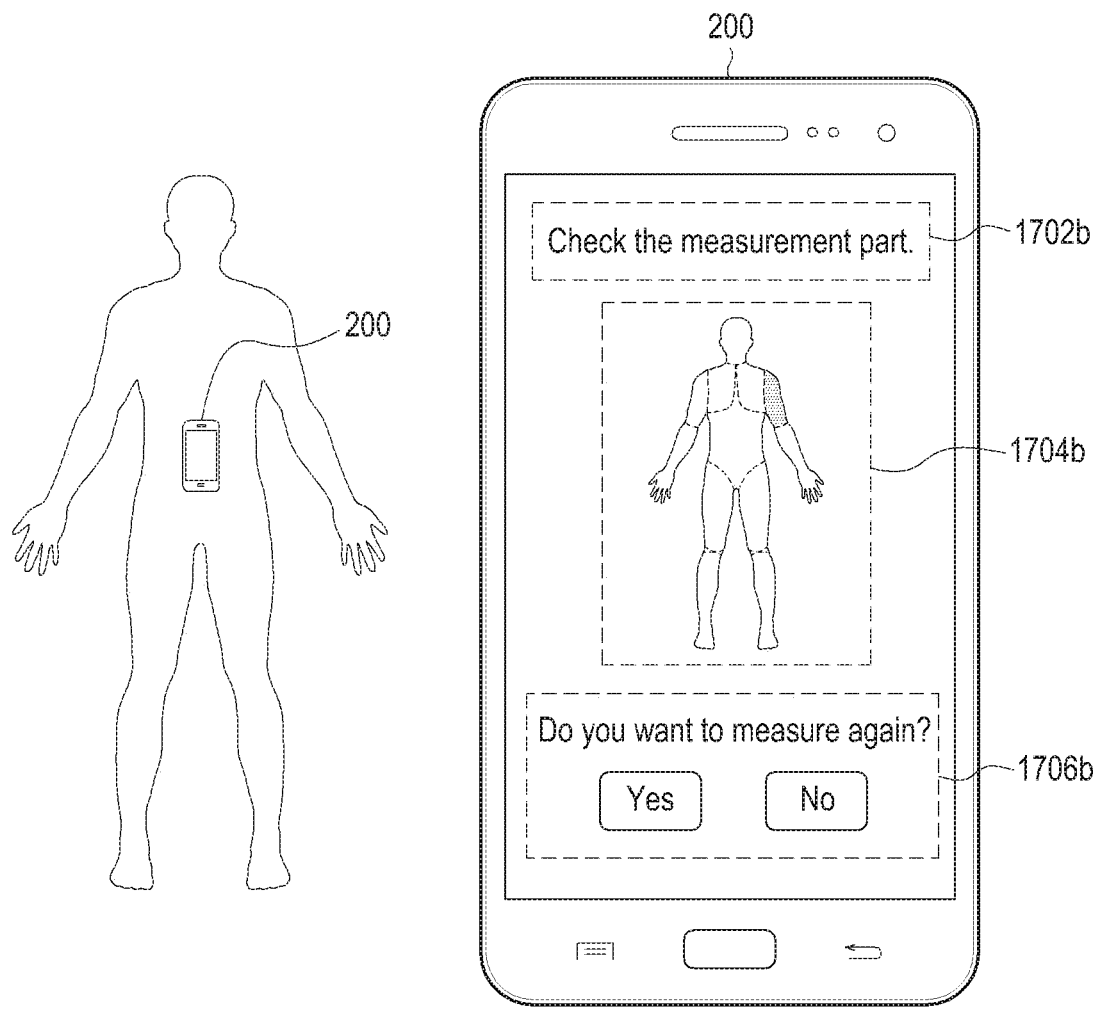

FIGS. 17A and 17B illustrate UI screens when a body composition is measured according to an embodiment of the present disclosure.

Referring to FIGS. 17A and 17B, they illustrate examples of the warning message and the measurement position guide screen displayed on the screen of the display unit 250 by the controller 280 in operations 1316 and 1516 when the voice recognized or the touch input measurement body part does not match the determined measurement body part. For example, it is assumed, in an embodiment of the present embodiment of the present disclosure, that the measurement body part, which is voice recognized or touch input by the user or the examinee, corresponds to the "left upper arm" and the measurement body part, which the user or the examinee brings the measurement electrodes A, B, C, and B into contact with corresponds to the "abdomen".

When the voice recognized or the touch input measurement body part does not match the determined measurement body part, the controller 280 may display a warning message and a measurement body part guide screen in various methods to allow the user or the examinee to recognize that the voice recognized or the touch input measurement body part (for example, the left upper arm) does not match the determined measurement body part (for example, the abdomen) according to an embodiment of the present disclosure.

First, as illustrated in FIG. 17A, when the voice recognized or the touch input measurement body part (for example, the left upper arm) does not match the determined measurement body part (for example, the abdomen) according to the embodiment of the present disclosure, the controller 280 may display both a warning message display area 1702a for instructing the user or the examinee to determine the measurement body part and the determined measurement body part (for example, the abdomen) in a measurement body part display area 1704a. In this case, the user or the examinee may identify the measurement body part display area 1704a and recognize that the user or the examinee has brought the measurement electrodes A, B, C, and D of the electronic device 200 into contact with the incorrect measurement body part, and may be induced to re-place the measurement electrodes A, B, C, and D of the electronic device 200 at the voice recognized or the touch input measurement body part. Although the measurement body part display area 1704a is displayed in the graphic form, the present disclosure is not limited thereto and the determined measurement body part may be displayed in a text form, such as the "abdomen".

Further, the controller 280 may also display a re-measurement message display area 1706a for asking about whether to re-perform the body composition measurement on the screen. When the user or the examinee presses a Yes button displayed in the re-measurement message display area 1706a, a re-measurement signal is generated and transmitted to the controller 280, and the controller 280 may return to operations 1306 and 1506 of FIGS. 13 and 15 according to the input re-measurement signal and repeatedly perform the following operations to measure the body composition of the voice recognized or the touch input measurement body part. When the user or the examinee presses a No button displayed in the re-measurement message display area 1706a, a re-measurement end signal is generated and transmitted to the controller 280, and the controller 280 may end the body composition measurement according to the input re-measurement end signal. For example, through the re-measurement message display area 1706a, the user or the examinee may be induced to re-place the measurement electrodes A, B, C, and D of the electronic device 200 at the voice recognized or the touch input measurement body part and to re-start the measurement of the body composition of the corresponding measurement body part.

Further, as illustrated in FIG. 17B, when the voice recognized or the touch input measurement body part does not match the determined measurement body part, the controller 280 may display both a warning message display area 1702b for instructing the user or the examinee to determine the measurement body part and the voice recognized or the touch input measurement body part (for example, the left upper arm) in a measurement body part display area 1704b. In this case, the user or the examinee may identify the measurement body part display area 1704b and recognize that the user or the examinee has brought the measurement electrodes A, B, C, and D of the electronic device 200 into contact with the incorrect measurement body part, and may be induced to re-place the measurement electrodes A, B, C, and D of the electronic device 200 at the voice recognized or the touch input measurement body part. Although the measurement body part display area 1704b is displayed in the graphic form, the present disclosure is not limited thereto and the voice recognized or the touch input measurement body part may be displayed in the text form, such as the "left upper arm".

Further, the controller 280 may also display a re-measurement identification display area 1706b for asking about whether to measure the body composition of the determined measurement body part on the screen. When the user or the examinee presses a Yes button displayed in the re-measurement identification display area 1706b, a measurement start signal is generated and transmitted to the controller 280, and the controller 280 may return to operations 1306 and 1506 of FIGS. 13 and 15 according to the received measurement start signal and repeatedly perform the following operations to measure the body composition of the determined measurement body part. When the user or the examinee presses a No button displayed in the re-measurement identification display area 1706b, a measurement end signal is generated and transmitted to the controller 280, and the controller 280 may end the measurement of the body composition of the determined measurement body part according to the received measurement end signal. For example, through the re-measurement identification display area 1706*b*, the user or the examinee may be induced to start the measurement of the body composition of the determined measurement body part.

Figure 18:
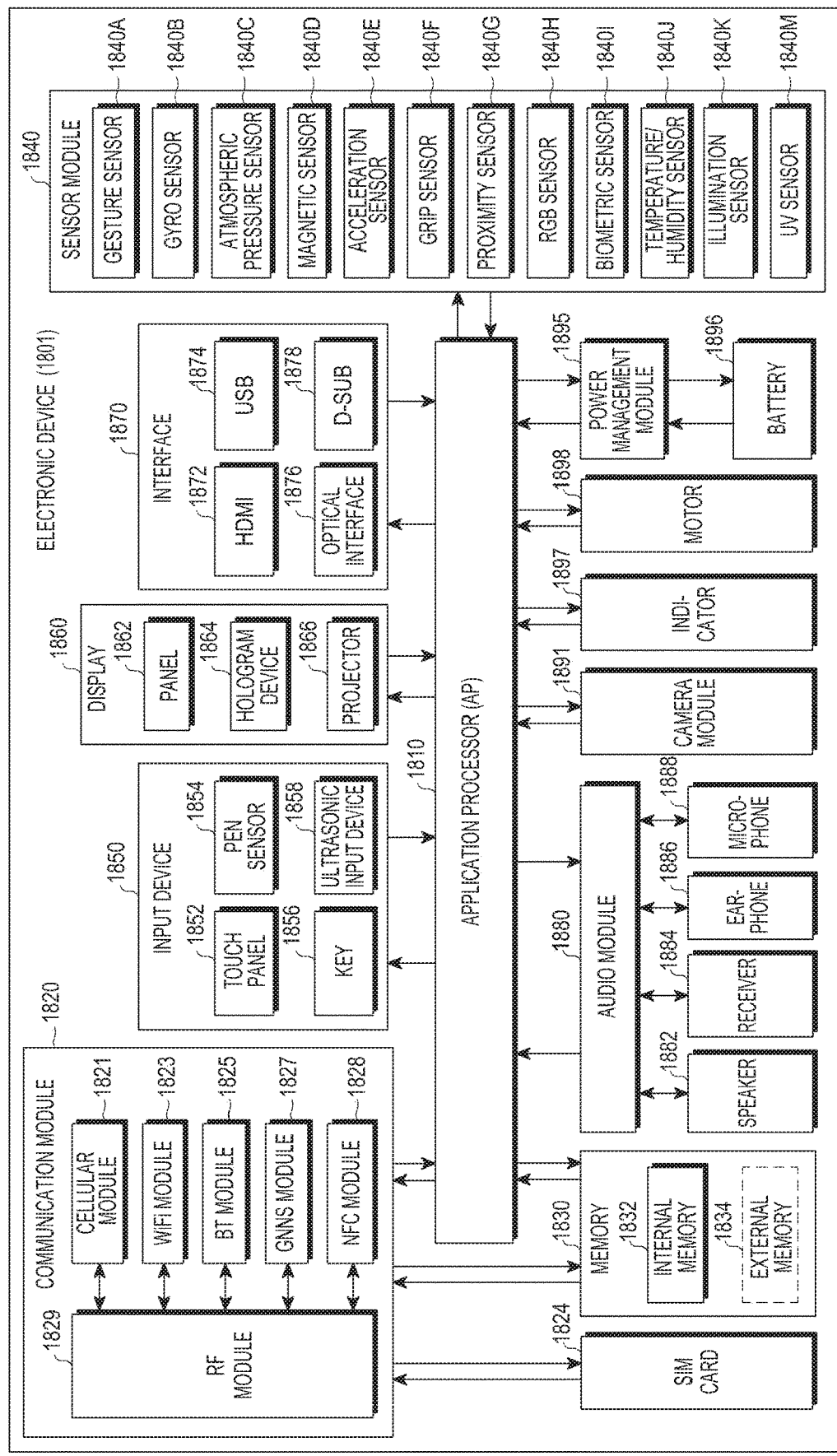
FIG. 18 is a block diagram illustrating an electronic device according to various embodiments of the present disclosure.

FIG. 18 is a block diagram of an electronic device according to various embodiments of the present disclosure.

Referring to FIG. 18, an electronic device 1801 may include, for example, the whole or part of the electronic device 101 illustrated in FIG. 1. The electronic device 1801 may include at least one AP 1810, a communication module 1820, a subscriber identification module 1824, a memory 1830, a sensor module 1840, an input device 1850, a display 1860, an interface 1870, an audio module 1880, a camera module 1891, a power management module 1895, a battery 1896, an indicator 1897, and a motor 1898.

The processor 1810 may control, for example, a plurality of hardware or software components connected to the processor 1810 by driving an operating system or an application program and perform processing of various pieces of data and calculations. The processor 1810 may be implemented by, for example, a system on chip (SoC). According to an embodiment of the present disclosure, the processor 1810 may further include a graphics processing unit (GPU) and/or an image signal processor. The processor 1810 may include at least some (for example, a cellular module 1821) of the elements illustrated in FIG. 18. The processor 1810 may load, into a volatile memory, instructions or data received from at least one (for example, a non-volatile memory) of the other elements and may process the loaded instructions or data, and may store various data in a non-volatile memory.

The communication module 1820 may have a configuration equal or similar to that of the communication interface 170 of FIG. 1. The communication module 1820 may include, for example, a cellular module 1821, a Wi-Fi module 1823, a BT module 1825, a GNSS module 1827 (for example, a GPS module, a Glonass module, a Beidou module, or a Galileo module), an NFC module 1828, and a RF module 1829.

The cellular module 1821 may provide a voice call, an image call, a text message service, or an Internet service through, for example, a communication network. According to an embodiment of the present disclosure, the cellular module 1821 may distinguish and authenticate electronic device within a communication network using the subscriber identification module 1824 (for example, a subscriber identification module (SIM) card). According to an embodiment of the present disclosure, the cellular module 1821 may perform at least some of the functions that the processor 1810 may provide. According to an embodiment of the present disclosure, the cellular module 1821 may include a CP.

Further, the cellular module 1821 may be implemented by, for example, an SoC. Although the elements, such as the cellular module 1821 (for example, the (CP)), the memory 1830, or the power management module 1895 are illustrated as elements separated from the processor 1810, the processor 1810 may include at least some of the above described elements (for example, the cellular module 1821) according to an embodiment of the present disclosure.

Each of the Wi-Fi module 1823, the BT module 1825, the GNSS module 1827, and the NFC module 1828 may include, for example, a processor for processing data transmitted and received through the relevant module. According to various embodiments of the present disclosure, at least some (for example, two or more) of the cellular module 1821, the Wi-Fi module 1823, the BT module 1825, the GNSS module 1827, and the NFC module 1828 may be included in one integrated chip (IC) or IC package.

The RF module 1829 may transmit/receive, for example, a communication signal (for example, an RF signal). The RF module 1829 may include, for example, a transceiver, a power amp module (PAM), a frequency filter, a low noise amplifier (LNA), or an antenna. According to an embodiment of the present disclosure, at least one of the cellular module 1821, the Wi-Fi module 1823, the BT module 1825, the GNSS module 1827, and the NFC module 1828 may transmit and receive RF signals through a separate RF module.

The subscriber identification module 1824 may include, for example, a card including a subscriber identity module and/or an embedded SIM, and may contain unique identification information (for example, an integrated circuit card identifier (ICCID)) or subscriber information (for example, an international mobile subscriber identity (IMSI)).

The memory 1830 (for example, the memory 130) may include, e.g., an internal memory 1832 or an external memory 1834. The internal memory 1832 may include at least one of, for example, a volatile memory (for example, a dynamic random access memory (DRAM), a static RAM (SRAM), a synchronous DRAM (SDRAM), and the like), a non-volatile memory (for example, a one time programmable read-only memory (OTPROM), a PROM, an erasable and PROM (EPROM), an electrically EPROM (EEPROM), a mask ROM, a flash ROM, a flash memory (for example, a not AND (NAND) flash memory, a not OR (NOR) flash memory, and the like), a hard drive, and a solid state drive (SSD).

The external memory 1834 may further include a flash drive, for example, a compact flash (CF), a secure digital (SD), a micro-SD (Micro-SD), a mini-SD (Mini-SD), an extreme digital (xD), a multi-media card (MMC), a memory stick, and the like. The external memory 1834 may be functionally and/or physically connected to the electronic device 1801 through various interfaces.

The sensor module 1840 may measure a physical quantity or detect an operation state of the electronic device 1801, and may convert the measured or detected information into an electrical signal. The sensor module 1840 may include, for example, at least one of a gesture sensor 1840A, a gyro sensor 1840B, an atmospheric pressure sensor 1840C, a magnetic sensor 1840D, an acceleration sensor 1840E, a grip sensor 1840F, a proximity sensor 1840G, a color sensor 1840H (for example, a red, green, blue (RGB) sensor), a biometric sensor 1840I, a temperature/humidity sensor 1840J, a light sensor 1840K, and a ultraviolet (UV) sensor 1840M. Additionally or alternatively, the sensor module 1840 may include, for example, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 1840 may further include a control circuit for controlling one or more sensors included therein. In various embodiments of the present disclosure, an electronic device 1801 may further include a processor configured to control the sensor module 1840 as a part of or separately from the processor 1810, and may control the sensor module 1840 while the processor 1810 is in a sleep state.

The input device 1850 may include, for example, a touch panel 1852, a (digital) pen sensor 1854, a key 1856, or an ultrasonic input device 1858. The touch panel 1852 may recognize a touch input in at least one of, for example, a capacitive type, a resistive type, an infrared type, and an ultrasonic wave type. In addition, the touch panel 1852 may further include a control circuit. The touch panel 1852 may further include a tactile layer and may provide a tactile response to the user.

The (digital) pen sensor 1854 may include, for example, a recognition sheet which is a part of the touch panel or is separated from the touch panel. The key 1856 may include, for example, a physical button, an optical key or a keypad. The ultrasonic input unit 1858 may detect an ultrasonic wave generated by an input means through a microphone (for example, the microphone 1888), and may confirm data corresponding to the detected ultrasonic wave.

The display 1860 (for example, the display 160) may include a panel 1862, a hologram device 1864 or a projector 1866. The panel 1862 may include a configuration identical or similar to that of the display 160 illustrated in FIG. 1. The panel 1862 may be implemented to be, for example, flexible, transparent, or wearable. The panel 1862 and the touch panel 1852 may be implemented as one module. The hologram 1864 may show a three dimensional image in the air by using an interference of light. The projector 1866 may display an image by projecting light onto a screen. The screen may be located, for example, inside or outside the electronic device 1801. According to an embodiment of the present disclosure, the display 1860 may further include a control circuit for controlling the panel 1862, the hologram device 1864, or the projector 1866.

The interface 1870 may include, for example, an HDMI 1872, a USB 1874, an optical interface 1876, or a d-sub-miniature (D-sub) 1878. The interface 1870 may be included in, for example, the communication interface 170 illustrated in FIG. 1. Additionally or alternatively, the interface 1870 may include, for example, a mobile high-definition link (MHL) interface, a SD card/MMC interface, or an IR data association (IrDA) standard interface.

The audio module 1880 may bilaterally convert, for example, a sound and an electrical signal. At least some elements of the audio module 1880 may be included in, for example, the input/output interface 150 illustrated in FIG. 1. The audio module 1880 may process sound information which is input or output through, for example, a speaker 1882, a receiver 1884, earphones 1886, the microphone 1888, and the like.

The camera module 1891 corresponds to, for example, a device capable of capturing a still image and a moving image. According to an embodiment of the present disclosure, the camera module 1891 may include one or more image sensors (for example, a front sensor or a back sensor), a lens, an image signal processor (ISP), and a flash (for example, an LED, a xenon lamp, and the like).

The power management module 1895 may manage, for example, power of the electronic device 1801. According to an embodiment of the present disclosure, the power management module 1895 may include a power management integrated circuit (PMIC), a charger integrated circuit (IC), or a battery or fuel gauge. The PMIC may use a wired and/or wireless charging method. Examples of the wireless charging method may include, for example, a magnetic resonance method, a magnetic induction method, an electromagnetic method, and the like. Additional circuits (for example, a coil loop, a resonance circuit, a rectifier, and the like) for wireless charging may be further included. The battery gauge may measure, for example, a residual quantity of the battery 1896, and a voltage, a current, or a temperature during the charging. The battery 1896 may include, for example, a rechargeable battery or a solar battery.

The indicator 1897 may display a particular state (for example, a booting state, a message state, a charging state, and the like) of the electronic device 1801 or a part (for example, the processor 1810) of the electronic device 1801. The motor 1898 may convert an electrical signal into mechanical vibration, and may generate vibration, a haptic effect, and the like. Although not illustrated, the electronic device 1801 may include a processing unit (for example, a GPU) for supporting a mobile television (TV). The processing unit for supporting mobile TV may, for example, process media data according to a certain standard, such as digital multimedia broadcasting (DMB), digital video broadcasting (DVB), or MediaFlo™.

Each of the above-described component elements of hardware according to the present disclosure may be configured with one or more components, and the names of the corresponding component elements may vary based on the type of electronic device. The electronic device according to various embodiments of the present disclosure may include at least one of the aforementioned elements. Some elements may be omitted or other additional elements may be further included in the electronic device. Further, some of the components of the electronic device according to the various embodiments of the present disclosure may be combined to form a single entity, and thus, may equivalently execute functions of the corresponding elements prior to the combination.

Figure 19:
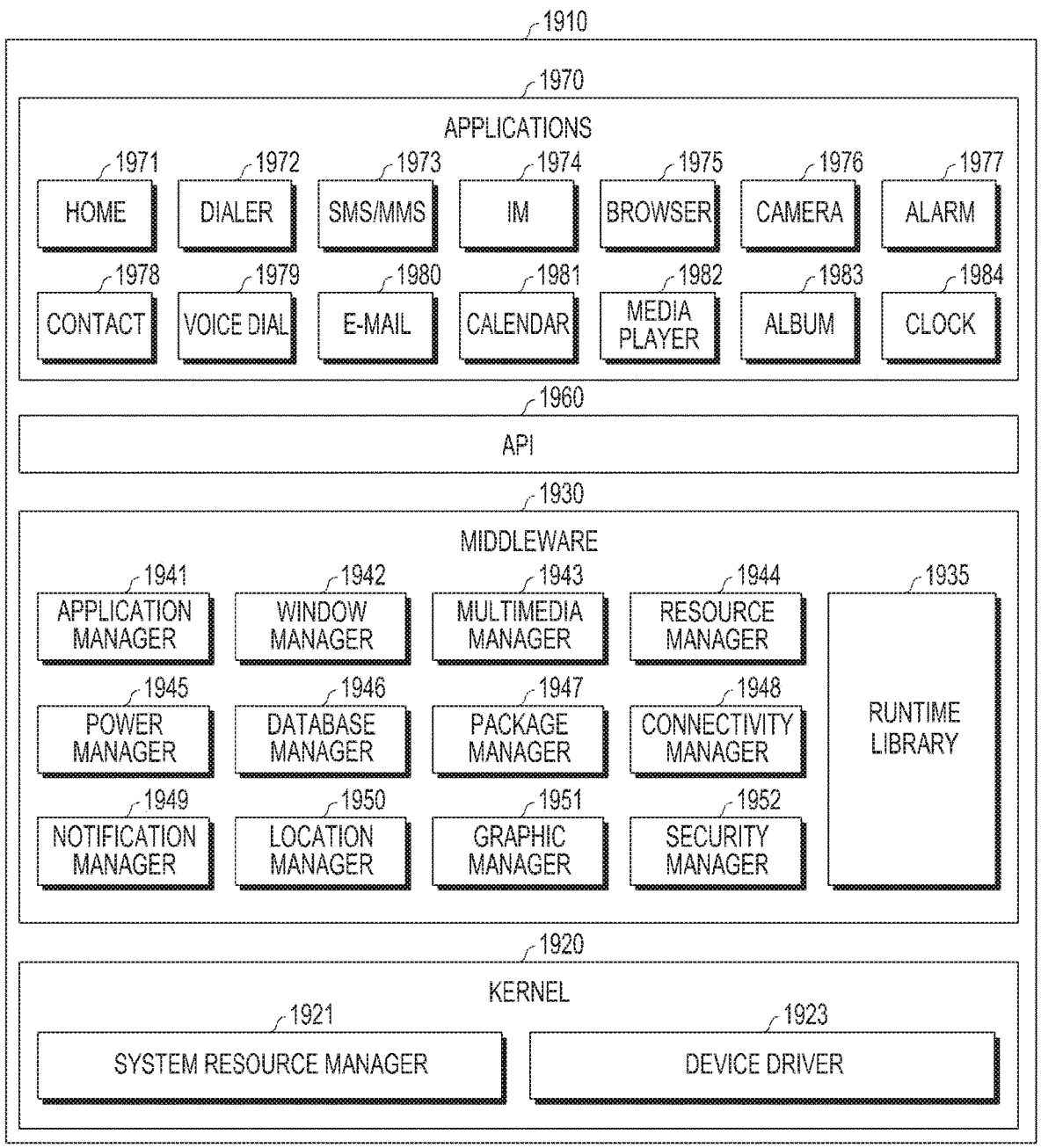
FIG. 19 is a block diagram illustrating a program module according to various embodiments of the present disclosure.

FIG. 19 is a block diagram illustrating a program module according to various embodiments of the present disclosure.

Referring to FIG. 19, a program module 1910 (for example, the program 140) may include an OS for controlling resources related to the electronic device (for example, the electronic device 101) and/or various applications (for example, the application program 147) executed in the OS. The OS may be, for example, Android, iOS, Windows, Symbian, Tizen, Bada, and the like.

The program module 1910 may include a kernel 1920, middleware 1930, an API 1960, and/or applications 1970. At least some of the program module 1910 may be preloaded on the electronic device, or may be downloaded from an external electronic device (for example, the first external electronic device 102, the second external electronic device 104, or the server 106).

The kernel 1920 (for example, the kernel 141) may include, for example, a system resource manager 1921 or a device driver 1923. The system resource manager 1921 may perform the control, allocation, retrieval, and the like, of system resources. According to an embodiment of the present disclosure, the system resource manager 1921 may include a process manager, a memory manager, or a file system manager. The device driver 1923 may include, for example, a display driver, a camera driver, a BT driver, a shared memory driver, a USB driver, a keypad driver, a Wi-Fi driver, an audio driver, or an inter-process communication (IPC) driver.

The middleware 1930 may provide a function required by the applications 1970 in common or provide various functions to the applications 1970 through the API 1960 so that the applications 1970 can efficiently use limited system resources within the electronic device. According to an embodiment of the present disclosure, the middleware 1930 (for example, the middleware 143) may include, for example, at least one of a runtime library 1935, an application manager 1941, a window manager 1942, a multimedia manager 1943, a resource manager 1944, a power manager 1945, a database manager 1946, a package manager 1947, a connectivity manager 1948, a notification manager 1949, a location manager 1950, a graphic manager 1951, and a security manager 1952.

The runtime library 1935 may include a library module which a compiler uses in order to add a new function through a programming language while the applications 1970 are being executed. The runtime library 1935 may perform input/output management, memory management, the functionality for an arithmetic function, and the like.

The application manager 1941 may manage, for example, a life cycle of at least one of the applications 1970. The window manager 1942 may manage graphical UI (GUI) resources used for the screen. The multimedia manager 1943 may determine a format required to reproduce various media files, and may encode or decode a media file by using a coder/decoder (codec) appropriate for the corresponding format. The resource manager 1944 may manage resources, such as a source code, a memory, a storage space, and the like, of at least one of the applications 1970.

The power manager 1945 may operate together with, for example, a basic input/output system (BIOS), and the like, and may manage a battery or power, and may provide power information, and the like, required for an operation of the electronic device. The database manager 1946 may generate, search for, or change a database to be used by at least one of the applications 1970. The package manager 1947 may manage the installation or update of an application distributed in the form of a package file.

The connectivity manager 1948 may manage a wireless connection, such as, for example, Wi-Fi or BT. The notification manager 1949 may display or notify of an event, such as an arrival message, an appointment, a proximity notification, and the like, in such a manner as not to disturb the user. The location manager 1950 may manage location information of the electronic device. The graphic manager 1951 may manage a graphic effect, which is to be provided to the user, or a UI related to the graphic effect. The security manager 1952 may provide various security functions required for system security, user authentication, and the like. According to an embodiment of the present disclosure, when the electronic device (for example, the electronic device 101) has a telephone call function, the middleware 1930 may further include a telephony manager for managing a voice call function or a video call function of the electronic device.

The middleware 1930 may include a middleware module that forms a combination of various functions of the above-described elements. The middleware 1930 may provide a module specialized for each type of OS in order to provide a differentiated function. In addition, the middleware 1930 may dynamically delete some of the existing elements, or may add new elements.

The API 1960 (for example, the API 145) corresponds to, for example, a set of API programming functions, and may be provided with a different configuration according to an OS. For example, in the case of Android or iOS, one API set may be provided for each platform. In the case of Tizen, two or more API sets may be provided for each platform.

The applications 1970 (for example, the application programs 147) may include, for example, one or more applications which can provide functions, such as a home application 1971, a dialer application 1972, a short message service (SMS)/multimedia message (MMS) application 1973, an instant message (IM) application 1974, a browser application 1975, a camera application 1976, an alarm application 1977, contacts application 1978, a voice dial application 1979, an email application 1980, a calendar application 1981, a media player application 1982, an album application 1983, a clock application 1984, a health care application (for example, measure exercise quantity or blood sugar), or environment information application (for example, atmospheric pressure, humidity, or temperature information).

According to an embodiment of the present disclosure, the applications 1970 may include an application (hereinafter, referred to as an "information exchange application" for convenience of description) supporting information exchange between the electronic device (for example, the electronic device 101) and an external electronic device (for example, the first external electronic device 102 or the second external electronic device 104). The information exchange application may include, for example, a notification relay application for transferring specific information to an external electronic device or a device management application for managing an external electronic device.

For example, the notification relay application may include a function of transferring, to the external electronic device (for example, the first external electronic device 102 or the second external electronic device 104), notification information generated from other applications of the electronic device (for example, an SMS/MMS application, an e-mail application, a health management application, or an environmental information application). Further, the notification relay application may receive notification information from, for example, an external electronic device and provide the received notification information to a user.

The device management application may manage (for example, install, delete, or update), for example, a function for at least a part of the external electronic device (for example, the first external electronic device 102 or the second external electronic device 104) communicating with the electronic device (for example, turning on/off the external electronic device itself (or some elements thereof) or adjusting brightness (or resolution) of a display), applications executed in the external electronic device, or services provided from the external electronic device (for example, a telephone call service or a message service).

According to an embodiment of the present disclosure, the applications 1970 may include applications (for example, a health care application of a mobile medical appliance, and the like) designated according to attributes of the external first external electronic device 102 or the second external electronic device 104. According to an embodiment of the present disclosure, the applications 1970 may include an application received from the external electronic device (for example, the server 106, or the first external electronic device 102 or the second external electronic device 104). According to an embodiment of the present disclosure, the applications 1970 may include a preloaded application or a third party application which can be downloaded from the server. Names of the elements of the program module 1910, according to the above-described embodiments of the present disclosure, may change depending on the type of OS.

According to various embodiments of the present disclosure, at least some of the program module 1910 may be implemented in software, firmware, hardware, or a combination of two or more thereof. At least some of the programming module 1910 may be implemented (for example, executed) by, for example, the processor (for example, the processor 1810). At least some of the program module 1910 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an application-specific integrated circuit (ASIC) chip, a field-programmable gate arrays (FPGA), and a programmable-logic device for performing operations which has been known or are to be developed hereinafter.

According to various embodiments of the present disclosure, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable storage medium may be, for example, the memory 130.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A portable electronic device for measuring biometric information, the portable electronic device comprising:
    at least one position-based sensor;
    a plurality of electrodes disposed on a first surface of the portable electronic device; and
    at least one processor configured to:
        identify, using the at least one position-based sensor, first position information of the portable electronic device when the portable electronic device is on a preset reference body part of an examinee,
        identify, using the at least one position-based sensor, second position information of the portable electronic device when the portable electronic device is on a first body part of the examinee, wherein the first body part of the examinee is different from the preset reference body part,
        obtain body fat measurement information based on signals from the plurality of electrodes in contact with the first body part of the examinee,
        identify a direction angle of the portable electronic device based on the first position information and the second position information, when the portable electronic device is on the first body part of the examinee,
        identify, from among a plurality of preset body parts, the first body part of the examinee on which the body fat measurement information is obtained, based on, at least, the first position information, the second position information, the direction angle of the portable electronic device and the body fat measurement information,
        identify, using the at least one position-based sensor, an average value of each of acceleration values, geomagnetic values, and altitude values during an initial setting time after the measurement starts, and
        set the average values as the first position information of the portable electronic device at the preset reference body part.

2. The portable electronic device of claim 1,
    wherein the at least one position-based sensor comprises at least one of an acceleration sensor, a geomagnetic sensor or an altimeter sensor, and
    wherein the at least one processor is further configured to:
        identify an acceleration value according to a movement of the portable electronic device from the preset reference body part to the first body part by using the acceleration sensor,
        identify geomagnetic values at the preset reference body part and the first body part by using the geomagnetic sensor, and
        identify altitude values at the preset reference body part and the first body part by using the altimeter sensor.

3. The portable electronic device of claim 1, wherein the at least one processor is further configured to:
    identify impedance and skin conductivity of the first body part, and
    identify a subcutaneous fat thickness of the first body part.

4. The portable electronic device of claim 1, wherein the at least one processor is further configured to:

identify a movement speed, a movement direction, or a movement distance of the portable electronic device from the preset reference body part to the first body part, based on the acceleration value according to the movement from the preset reference body part to the first body part, identify the direction angle of the portable electronic device at the first body part moved from the preset reference body part, based on the average geomagnetic value at the preset reference body part and the geomagnetic value at the first body part, identify an altitude of the portable electronic device at the first body part moved from the preset reference body part, based on the average altitude value at the preset reference body part and the altitude value at the first body part, and identify a position and the direction angle of the portable electronic device at the first body part, based on at least one of the movement speed, movement direction, movement distance, or altitude of the portable electronic device at the first body part.

5. The portable electronic device of claim 1, wherein the at least one processor is further configured to:

compare the body fat measurement information with each of a plurality of pre-stored body part-specific body fat-based standard ranges, and identify the at least one candidate body part having the body fat measurement information, which is included in the plurality of pre-stored body part specific body fat-based standard ranges among the plurality of preset body parts.

6. The portable electronic device of claim 5, wherein the at least one processor is further configured to:

compare an impedance value of the body fat measurement information with a body part-specific impedance standard range among the plurality of pre-stored body part-specific body fat-based standard ranges and identify at least one first candidate body part having the detected impedance value, which corresponds to the body part-specific impedance standard range, among the plurality of preset body parts, compare a subcutaneous fat thickness of the body fat measurement information with a body part-specific subcutaneous fat standard range among the plurality of pre-stored body part-specific body fat-based standard ranges and identify at least one second candidate body part having the detected subcutaneous fat thickness, which corresponds to the body part-specific subcutaneous fat standard range, among the plurality of preset body parts, compare a skin conductivity value of the body fat measurement information with a body part-specific skin conductivity standard range among the plurality of pre-stored body part-specific body fat-based standard ranges and identify at least one third candidate body part having the detected skin conductivity value, which corresponds to the body part-specific skin conductivity standard range, among the plurality of preset body parts, and identify at least one body part, which are included in the at least one first to third candidate body parts in common, as the at least one candidate body part corresponding to the first body part.

7. The portable electronic device of claim 6, wherein the at least one processor is further configured to:

identify a left and right position of the portable electronic device at the first body part moved from the preset reference body part, based on a movement speed, a movement direction, and a movement distance of the portable electronic device from the preset reference body part to the first body part, identify a front and back position of the portable electronic device at the first body part, based on a direction angle of the portable electronic device at the first body part moved from the preset reference body part, identify an up and down position of the portable electronic device at the first body part, based on an altitude of the portable electronic device at the first body part moved to from the preset reference body part, and identify, as the first body part corresponding to the first body part, a candidate body part corresponding to the identified left and right position, front and back position, and up and down position based on the reference body part corresponding to the preset reference body part, from among the at least one candidate body part.

8. A method of measuring biometric information by an electronic device, the method comprising:

identifying, using at least one position-based sensor, first position information of the portable electronic device when the portable electronic device is on a preset reference body part of an examinee;

identifying, using the at least one position-based sensor, second position information of the portable electronic device when the portable electronic device is on a first body part of the examinee, wherein the first body part of the examinee is different from the preset reference body part;

obtaining body fat measurement information based on signals from the plurality of electrodes in contact with the first body part of the examinee;

identifying a direction angle of the portable electronic device based on the first position information and the second position information, when the portable electronic device is on the first body part of the examinee;

identifying, from among a plurality of preset body parts, the first body part of the examinee on which the body fat measurement information is obtained, based on, at least, the first position information, the second position information, the direction angle of the portable electronic device and the body fat measurement information;

identifying, using the at least one position-based sensor, an average value of each of acceleration values, geomagnetic values, and altitude values during an initial setting time after the measurement starts; and setting the average values as the first position information of the portable electronic device at the preset reference body part.

9. The method of claim 8, wherein the at least one position-based sensor comprises at least one of an acceleration sensor, a geomagnetic sensor or an altimeter sensor, and wherein the method further comprises:

identifying an acceleration value according to a movement of the portable electronic device from the preset reference body part to the first body part by using the acceleration sensor;

identifying geomagnetic values at the preset reference body part and the first body part by using the geomagnetic sensor; and identifying altitude values at the preset reference body part and the first body part by using the altimeter sensor.

10. The method of claim 8,
identifying impedance and skin conductivity of the first body part; and
identifying a subcutaneous fat thickness of the first body part.

11. The method of claim 8, further comprising:
identifying a movement speed, a movement direction, or a movement distance of the portable electronic device from the preset reference body part to the first body part, based on the acceleration value according to the movement from the preset reference body part to the first body part;
identifying the direction angle of the portable electronic device at the first body part moved from the preset reference body part, based on the average geomagnetic value at the preset reference body part and the geomagnetic value at the first body part;
identifying an altitude of the portable electronic device at the first body part moved from the preset reference body part, based on the average altitude value at the preset reference body part and the altitude value at the first body part; and
identifying a position and the direction angle of the portable electronic device at the first body part, based on at least one of the movement speed, movement direction, movement distance, or altitude of the portable electronic device at the first body part.

12. The method of claim 8, further comprising:
comparing the body fat measurement information with each of a plurality of pre-stored body part-specific body fat-based standard ranges; and
identifying the at least one candidate body part having the body fat measurement information, which is included in the plurality of pre-stored body part specific body fat-based standard ranges among the plurality of preset body parts.

13. The method of claim 12, further comprising:
comparing an impedance value of the body fat measurement information with a body part-specific impedance standard range among the plurality of pre-stored body part-specific body fat-based standard ranges and identify at least one first candidate body part having the detected impedance value, which corresponds to the body part-specific impedance standard range, among the plurality of preset body parts;
comparing a subcutaneous fat thickness of the body fat measurement information with a body part-specific subcutaneous fat standard range among the plurality of pre-stored body part-specific body fat-based standard ranges and identify at least one second candidate body part having the detected subcutaneous fat thickness, which corresponds to the body part-specific subcutaneous fat standard range, among the plurality of preset body parts;
comparing a skin conductivity value of the body fat measurement information with a body part-specific skin conductivity standard range among the plurality of pre-stored body part-specific body fat-based standard ranges and identify at least one third candidate body part having the detected skin conductivity value, which corresponds to the body part-specific skin conductivity standard range, among the plurality of preset body parts; and
identifying at least one body part, which are included in the at least one first to third candidate body parts in common, as the at least one candidate body part corresponding to the first body part.

14. At least one non-transitory machine-readable storage medium for storing a computer program of instructions configured to be readable by at least one processor for instructing the at least one processor to execute a computer process for performing the method of claim 8.

* * * * *